(12) United States Patent
McCann et al.

(10) Patent No.: US 11,439,714 B2
(45) Date of Patent: Sep. 13, 2022

(54) RADIOPHARMACEUTICAL AND METHODS

(71) Applicant: Centre for Probe Development and Commercialization (CPDC), Hamilton (CA)

(72) Inventors: Joe McCann, Toronto (CA); Justyna Kelly, Cambridge (CA); Paul Billone, Dundas (CA)

(73) Assignee: Centre for Probe Development and Commercialization, Hamilton (CA)

( * ) Notice: Subject to any disclaimer, the term of this patent is extended or adjusted under 35 U.S.C. 154(b) by 0 days.

(21) Appl. No.: 17/461,860

(22) Filed: Aug. 30, 2021

(65) Prior Publication Data

US 2022/0062447 A1    Mar. 3, 2022

Related U.S. Application Data

(63) Continuation of application No. PCT/IB2021/000589, filed on Aug. 27, 2021.

(60) Provisional application No. 63/071,138, filed on Aug. 27, 2020.

(51) Int. Cl.
| | |
|---|---|
| *A61K 51/00* | (2006.01) |
| *A61M 36/14* | (2006.01) |
| *A61K 51/04* | (2006.01) |
| *A61K 51/12* | (2006.01) |
| *A61K 47/12* | (2006.01) |
| *A61K 47/02* | (2006.01) |
| *A61K 47/22* | (2006.01) |
| *A61K 9/00* | (2006.01) |

(52) U.S. Cl.
CPC .......... *A61K 51/0482* (2013.01); *A61K 47/02* (2013.01); *A61K 47/12* (2013.01); *A61K 47/22* (2013.01); *A61K 51/121* (2013.01); *A61K 9/0019* (2013.01)

(58) Field of Classification Search
None
See application file for complete search history.

(56) References Cited

U.S. PATENT DOCUMENTS

| | | | |
|---|---|---|---|
| 1,096,278 | A | 5/1914 | Sutton |
| 6,261,536 | B1 | 7/2001 | Zamora et al. |
| 10,596,276 | B2 | 3/2020 | De Palo et al. |
| 10,596,278 | B2 | 3/2020 | De Palo et al. |
| 2007/0269375 | A1 | 11/2007 | Chen et al. |
| 2008/0077128 | A1 | 3/2008 | Woloszko et al. |
| 2012/0065365 | A1 | 3/2012 | Chen et al. |
| 2015/0094710 | A1 | 4/2015 | Edwards et al. |
| 2018/0049832 | A1 | 2/2018 | Eckert et al. |
| 2018/0168734 | A1 | 6/2018 | Strobl |
| 2020/0038121 | A1 | 2/2020 | Yang et al. |

FOREIGN PATENT DOCUMENTS

| | | |
|---|---|---|
| CA | 2989266 A1 | 12/2016 |
| WO | 2020/088767 A1 | 5/2020 |

OTHER PUBLICATIONS

Thisgaard et al. (J. Nucl. Med. 2014, 55, 1311-1316).*
Das et al. (Cancer Biother. Radiopharm. 2011, 26, 395-400).*
Kunikowska et al. (Eur. J. Nucl. Med. Imaging 2011, 38, 1788-1797).*
(2006), 177Lu—Dotatate Phase 3 Trial in Midgut Neuroendocrine Tumors, Supplementary Appendix, 15 pages.
Zaknun et al. (May 2013) "The Joint IAEA, EANM, and SNMMI Practical Guidance on Peptide Receptor Radionuclide Therapy (PRRNT) in Neuroendocrine Tumours", European Journal of Nuclear Medicine and Molecular Imaging, 40:800-816.
(Apr. 14, 2021) Decision Denying Institution of Post Grant Review 35 U.S.C § 325 (d) for U.S. Pat. No. 10,596,276, Case No. PGR2021-00003, 20 pages.
(Apr. 14, 2021) Decision Denying Institution of Post-Grant Review 35 U.S.C.§ 325 (d) for U.S. Pat. No. 10,596,278, Case No. PGR2021-00002, 17 pages.
Declaration of Ingrid Hsieh Yee, PH.D in support of Petition for Post Grant Review of U.S. Pat. No. 10,596,278, Case No. PGR2021-00002, 279 pages.
Declaration of Stephen Maus Under 37 CFR § 1.68 in Support of Petition for Post Grant Review of U.S. Pat. No. 10,596,276, Case No. PGR2021-00003, 224 pages.
Explanation of Multiple Petitions Challenging the Same Patent in Accordance With Jul. 2019 Updated Patent Trial Guide for U.S. Pat. No. 10,596,278, Case No. PGR2021-00002, 6 pages.
Patent Owner Response to Petitioner's Explanation of Parallel petitions for U.S. Pat. No. 10,596,278, Case No. PGR2021-00002, 7 pages.
Petition for Post Grant Review of U.S. Pat. No. 10,596,276, Case No. PGR2021-00003, 101 pages.
Petition for Post Grant Review of U.S. Pat. No. 10,596,278, Case No. PGR2021-00002, 97 pages.
Petitioner's Authorized Reply to Patent Owner's Preliminary Response for U.S. Pat. No. 10596276, Case No. PGR2021-00003, 7 pages.
Preliminary Patent Owner Response for U.S. Pat. No. 10,596,276, Case No. PGR2021-00003, 91 pages.
Preliminary Patent Owner Response for U.S. Pat. No. 10,596,278, Case No. PGR2021-00002, 59 pages.
Publication Process, The New England Journal of Medicine, 2005, 27 pages.
Aslani et al. (2015) "Lutetium-177 DOTATATE Production with an Automated Radiopharmaceutical Synthesis System", Asia Oceania Journal of Nuclear Medicine and Biology, 3(2):107-115.
Banerjee et al. (Apr. 22, 2015) "Lutetium-177 Therapeutic Radiopharmaceuticals: Linking Chemistry, Radiochemistry, and Practical Applications", Chemical Reviews, 115(8):2934-2974.
Breeman et al. (Jun. 2003) "Optimising Conditions for Radiolabelling of DOTA-Peptides with 90Y, 111In and 177Lu at High Specific Activities", European Journal of Nuclear Medicine and Molecular Imaging, 30(6):917-920.

(Continued)

*Primary Examiner* — Michael G. Hartley
*Assistant Examiner* — Melissa J Perreira
(74) *Attorney, Agent, or Firm* — Fox Rothschild LLP

(57) ABSTRACT

A radiopharmaceutical $^{177}$Lu-DOTATATE compound, a composition, and a kit are provided. Further provided are methods of synthesis of a $^{177}$Lu-DOTATATE compound and methods of treatment that comprise a $^{177}$Lu-DOTATATE compound.

17 Claims, 5 Drawing Sheets

(56) References Cited

OTHER PUBLICATIONS

Breeman et al. (2016) "Overview of Development and Formulation of [1] Lu-DOTA-TATE for PRRT", Current Radiopharmaceuticals, 9(1):8-18.
Breeman et al. (Feb. 2003) "The Addition of DTPA to [177Lu-DOTA0,tyr3]octreotate Prior to Administration Reduces Rat Skeleton Uptake of Radioactivity", European Journal of Nuclear Medicine and Molecular Imaging, 30(2):312-315.
Chen et al. (Apr. 2008) "Synthesis, stabilization and formulation of [177Lu]Lu-AMBA, a systemic radiotherapeutic agent for Gastrin Releasing Peptide receptor positive tumors", Applied Radiation and Isotopes, 66(4):497-505.
Das et al. (Sep. 2014) "Formulation of Patient Dose of [1] Lu-DOTA-TATE in Hospital Radiopharmacy in India: Preparation using in Situ Methodology vis-a-vis Freeze-dried Kit", Cancer Biotherapy and Radiopharmaceuticals, 29(7):301-302.
Das et al. (Mar. 2007) "On the Preparation of a Therapeutic Dose of 177Lu-labeled DOTA-TATE using Indigenously Produced 177Lu in Medium Flux Reactor", Applied Radiation and Isotopes, 65(3):301-308.
Das, et al. (Jan. 4, 2014) "Preparation of DOTA-TATE and DOTA-NOC freeze-dried kits for formulation of patient doses of 177Lu-labeled agents and their comparison for peptide receptor radionuclide therapy application", Journal of Radioanalytical and Nuclear Chemistry, 299:1389-1398.
De Leon-Rodriguez et al. (Feb. 2008) "The Synthesis and Chelation Chemistry of DOTA-Peptide Conjugates", A Publication of the American Chemical Society, 19(2):391-580 (20 pages).
Deblois et al. (Feb. 2014) "Application of Single-Vial Ready-for-Use Formulation of 111In- or 177Lu-Labelled Somatostatin Analogs", Applied Radiation and Isotopes, 85:28-33.
Flice et al. (2012) "Radiolabeled Somatostatin Analogues Therapy in Advanced Neuroendocrine Tumors: A Single Centre Experience", Journal of Oncology, 2012: 320198 (10 pages).
Frilling et al. (Dec. 2006) "Treatment with 90Y- and 177Lu-DOTATOC in Patients with Metastatic Neuroendocrine Tumors", Surgery, 140(6):968-977.
Kwekkeboom et al. (Sep. 2001) "[177Lu-DOTA0,Tyr3]octreotate: comparison with [111In-DTPA0]octreotide in patients", European Journal of Nuclear Medicine, 28(9):1319-1325 (8 pages).
Liu et al. (Sep.-Oct. 2003) "Ascorbic Acid: Useful as a Buffer Agent and Radiolytic Stabilizer for Metalloradiopharmaceuticals", Bioconjugate Chemistry, 14(5):1052-1056.
Liu et al. (Jul.-Aug. 2001) "Stabilization of (90)y-labeled DOTA-biomolecule Conjugates using Gentisic Acid and Ascorbic Acid", Bioconjugate Chemistry, 12(4):554-558.
Luna-Gutie'rrez et al. (Aug. 29, 2017) "Freeze-dried multi-dose kits for the fast preparation of 177Lu-Tyr3-octreotide and 177Lu-PSMA(inhibitor) under GMP conditions", Journal of Radioanalytical and Nuclear Chemistry, 8 pages.

Maus et al. (Feb. 2014) "Aspects on Radiolabeling of 177Lu-DOTA-TATE: After C18 Purification Re-Addition of Ascorbic Acid is Required to Maintain Radiochemical Purity", International Journal of Diagnostic Imaging, 1(1):5 (8 pages).
Pop et al. (Nov. 3, 2015) "Use and Mis-use of Supplementary Material in Science Publications", BMC Bioinformatics, 16:237 (4 pages).
Price et al. (Sep. 24, 2018) "Role of Supplementary Material in Biomedical Journal Articles: Surveys of Authors, Reviewers and Readers", BMJ Open, 7 pages.
Scott et al. (Jan. 2009) "Studies Into Radiolytic Decomposition of Fluorine-18 Labeled Radiopharmaceuticals for Positron Emission Tomography", Applied Radiation and Isotopes, 67(1):88-94.
Sosabowski et al. (2006) "Conjugation of Dota-like Chelating Agents to Peptides and Radiolabeling With Trivalent Metallic Isotopes", Nature Protocols, 1(2):972-976.
Strosberg et al. (Jan. 12, 2017) "Phase 3 Trial of 177 Lu-Dotatate for Midgut Neuroendocrine Tumors", The New England Journal of Medicine, 376(2):125-135 (64 pages).
Lambert J. William (Sep. 2010) "Considerations in Developing a Target Product Profile for Parenteral Pharmaceutical Products", AAPS PharmSciTech, 11(3):1476-1481.
Maqsood M, et al; Neuroendocrine Tumor Therapy with Lutetium-177: A Literature Review. Cureus Jan. 30, 2019; 11 (1): e3986. DOO 10. 7759/cureus.3986, 7 pages.
B.L. R. Kam et al.; Lutetium-labelled peptides for therapy of neuroendocrine tumors; Eur J Nucl Med Mol Imaging (2012)39 (Suppl 1):S103-S112.
Ute Hennrich; Lutathera®: The First FDA- and EMA-Approved Radiopharmaceutical for Peptide Receptor Radionuclide Therapy; Jul. 29, 2019; 12; 114, 8 pages.
Mukherjee et al.: Single vial kit formulation of DOTATATE for preparation of 177 Lu-labeled therapeutic radiopharmaceutical at hospital radiopharmacy; J. Label Compd. Radiopharm.; 2015; 58 166-172.
Estephany Abou Jokh Casas et al.: Evaluation of 177Lu-Dotatate treatment in patients with metastatic neuroendocrine tumors and prognostic factors; World J Gastroenterol; Apr. 7, 2020; 26(13); 1513-1524.
Ulrika Jahn: 177Lu-DOTATATE Peptide Receptor Radionuclide Therapy: Dose Response in Small Intestinal Neuroendocrine Tumors Neuroendocrinology; 2020; 110; pp. 662-670.
Ashutosh Dash et al.: Peptide Receptor Radionuclide Therapy:An Overview; Cancer Biotherapy and Radiopharmaceuticals; 2015; vol. 30, No. 2, pp. 47-71.
Brian J. Burkett: A Multidisciplinary Approach to 177Lu DOTATATE Peptide Receptor Radionuclide Therapy; Radiology; 2021; 298; 261-274.
International Search Report and Written Opinion dated Feb. 25, 2022 in International Application No. PCT/IB2021/000589, 14 pages.

* cited by examiner

RADIOPHARMACEUTICAL AND METHODS

This application is a continuation application of International Application No. PCT/IB2021/000589, filed Aug. 27, 2021, which claims the benefit of U.S. patent application Ser. No. 63/071,138 filed Aug. 27, 2020, both of which applications are incorporated by reference herein in its entirety.

FIELD

The radiopharmaceutical $^{177}$Lu-DOTATATE ($^{177}$Lu-octreotate) and a pharmaceutical composition thereof are provided. Further provided are methods of preparing $^{177}$Lu-DOTATATE compound and pharmaceutical compositions that include $^{177}$Lu-DOTATATE.

BACKGROUND

Radiopharmaceuticals have been used for a variety of therapeutic and diagnostic indications. Among others, radiolabeled molecules have been useful to treat various malignant tumors.

Use of these agents presents certain challenges, including with respect to stability and shelf-life. In particular, therapeutic compositions comprising a radionuclide may undergo radiolysis during preparation and storage. During radiolysis, radionuclide emissions may react with other groups of the pharmaceutical agent thereby resulting in decomposition of the agent as well as undesired effects.

It thus would be desirable to have additional and improved radiopharmaceutical agents.

SUMMARY

We now provide, inter alia, radiopharmaceutical $^{177}$Lu-DOTATATE compound, methods of preparing the compound, and pharmaceutical compositions and methods of treatment including $^{177}$Lu-DOTATATE.

We have now found, inter alia, 1) new methods to produce high purity $^{177}$Lu-DOTATATE including with high levels of $^{177}$Lu incorporation, mild reaction temperatures and/or reduced reaction times and 2) new $^{177}$Lu-DOTATATE pharmaceutical compositions that maintain radiochemical purity for extended storage times following preparation (e.g. >90 or 95%, 3, 4 or 5 days or more, 25° C.). See, for instance, the results of the Examples which follow.

The preferred methods and pharmaceutical compositions include relatively high amounts of one or more stabilizers, particularly high amounts of one or more ascorbate compounds and/or one or more gentisate compounds.

More particularly, pharmaceutical compositions are provided that comprise: (a) a complex of lutetium-177 and tetraazacyclododecane tetra-acetic acid-octreotate (DOTATATE); and (b) one or more stabilizer compounds in a concentration of at least 25 mg/mL.

In certain aspects, suitably, the complex of lutetium-177 and tetraazacyclododecane tetra-acetic acid-octreotate (DOTATATE) is present in an amount of at least 5, 10, 15, 20, 25 or 30 mCi/mL.

In certain aspects, the one or more stabilizers comprise one or more ascorbate compounds.

In certain aspects, the one or more stabilizers comprise one or more gentisate compounds.

In certain preferred aspects, the pharmaceutical composition comprises two or more distinct stabilizers. In particular preferred aspects, the pharmaceutical composition comprises stabilizers that include at least one ascorbate compound and at least one gentisate compound.

In certain preferred aspects, one or more stabilizer compounds are present in a pharmaceutical composition in an amount of 30 mg/mL or greater.

In certain preferred aspects, one or more stabilizer compounds are present in a pharmaceutical composition in an amount of 40 mg/mL or greater.

In certain preferred aspects, one or more stabilizer compounds are present in a pharmaceutical composition in an amount of 50 mg/mL or greater.

In certain preferred aspects, one or more stabilizer compounds are present in a pharmaceutical composition in an amount of from about 25, 30, 35 or 40 mg/mL to 45, 50, 55, 60, 65, 70, 75 or 80 mg/mL.

In certain preferred aspects, a pharmaceutical composition comprises two distinct stabilizers, particularly 1) an ascorbate compounds such as an ascorbate salt and/or ascorbic acid and 2) a gentisate compound such as gentisic acid.

Suitably, the pharmaceutical composition is an aqueous formulation. In certain preferred aspects, a pharmaceutical composition does not contain an alcohol such as ethanol or other organic solvent. In certain preferred aspects, a pharmaceutical composition is at least substantially free (i.e. less than 5, 4, 3, 2, 1 or 0.5 weight percent based on total composition weight) of an alcohol such as ethanol or other organic solvent.

The compound tetraazacyclododecane tetra-acetic acid-octreotate (DOTATATE) has the following structure 1:

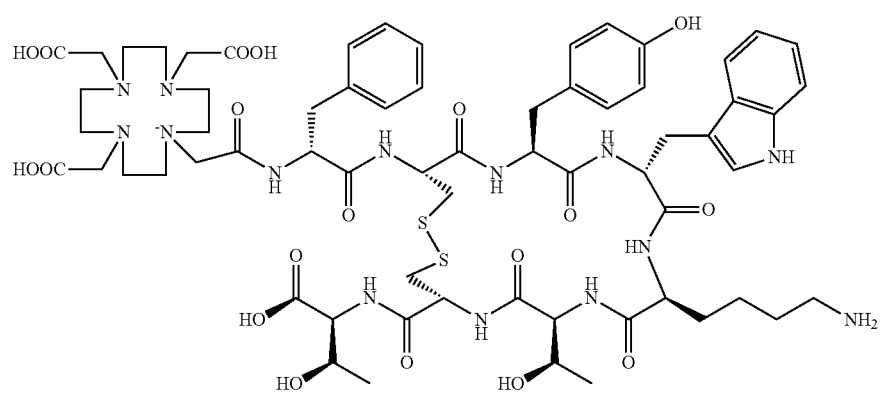

$^{177}$Lu-DOTATATE is a lutetium-177 complex of the above compound 1 and may be represented by the following structure 2:

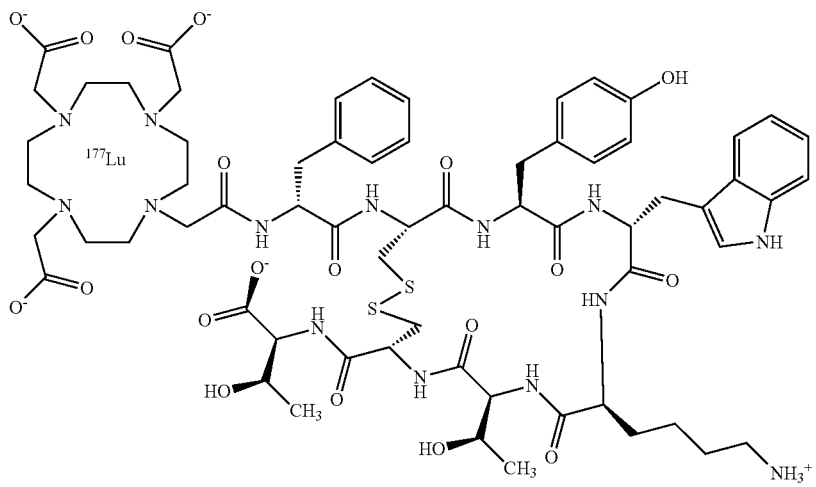

2

In an aspect, methods are provided for preparing $^{177}$Lu-DOTATATE (structure 2 above), which includes admixing lutetium-177 and tetraazacyclododecane tetra-acetic acid-octreotate (DOTATATE, structure 1 above) in the presence of one or more stabilizer compounds and forming a complex of $^{177}$Lu and DOTATATE. This reaction to form a complex of $^{177}$Lu and DOTATATE (e.g. such complex including structure 2 above) that may include admixing $^{177}$Lu and DOTATATE is sometimes referred to herein as an "incorporation reaction".

The one or more stabilizer compounds are suitably present in an incorporation reaction and/or a pharmaceutical composition in an amount of 7 mg/mL or greater, including 8, 9, 10, 11, 12, 13, 14, 15, 20, 25, 30, 35, 40, 45 or 50 mg/mL or greater.

In preferred aspects, the tetraazacyclododecane tetra-acetic acid-octreotate (DOTATATE) is admixed with lutetium-177 as an aqueous formulation.

In further preferred aspects, the one or more stabilizer compounds are present in an incorporation reaction and/or a pharmaceutical composition in an amount of 12, 15, 20 or 25 mg/mL or greater. In certain aspects, the one or more stabilizer compounds are present in an incorporation reaction and/or a pharmaceutical composition in an in an amount of 30 mg/mL or greater. In additional aspects, the one or more stabilizers are present in an incorporation reaction and/or a pharmaceutical composition in an in an amount of 40 mg/mL or greater. In still further aspects, the one or more stabilizers are present in an incorporation reaction and/or a pharmaceutical composition in an in an amount of 50 mg/mL or greater.

In certain preferred aspects, each of two or more distinct stabilizer compounds are present in an incorporation reaction and/or a pharmaceutical composition in an amount of 10 mg/mL or greater.

In certain preferred aspects, the one or more stabilizers present in an incorporation reaction and/or a pharmaceutical composition include one or more ascorbate compounds. In certain preferred aspects, the one or more stabilizers present in an incorporation reaction and/or a pharmaceutical composition comprise one or more gentisate compounds.

In certain preferred aspects, the one or more stabilizers present in an incorporation reaction and/or a pharmaceutical composition include one or more gentisate compounds in an amount of at least 7, 8, 9 or 10 mg/mL and one or more ascorbate compounds in an amount of at least 15, 20, 25 or 30 mg/mL, or one or more gentisate compounds in an amount of at least 15 mg/mL and one or more ascorbate compounds in an amount of at least 40 mg/mL.

In certain aspects, at least one of the stabilizers present in an incorporation reaction and/or a pharmaceutical composition is an ascorbate compounds, particularly an ascorbate salt such as sodium ascorbate.

Preferably, prior to the incorporation reaction or addition to $^{177}$Lu-DOTATATE to provide a pharmaceutical composition, the ascorbate compound such as sodium ascorbate is assessed for purity or absence of a material that may inhibit the incorporation reaction of lutetium-177 and tetraazacyclododecane tetra-acetic acid-octreotate (DOTATATE). For instance, a sample from a lot of an ascorbate compound such as an ascorbate metal salt e.g. sodium ascorbate can be tested such as in a test-scale (small-scale) incorporation reaction of lutetium-177 and tetraazacyclododecane tetra-acetic acid-octreotate (DOTATATE) to ensure the ascorbate compound lot does not adversely impact the formation of the complex of lutetium-177 and tetraazacyclododecane tetra-acetic acid-octreotate (DOTATATE) or the radiochemical stability of the formed complex over time.

Accordingly, methods are provided that comprise determining purity of an ascorbate compound prior to admixing the ascorbate compound with lutetium-177 and/or tetraazacyclododecane tetra-acetic acid-octreotate (DOTATATE) and/or a complex of lutetium-177 and/or tetraazacyclododecane tetra-acetic acid-octreotate (DOTATATE). Suitably, the ascorbate compound is determined to be effective in an incorporation reaction and method comprises admixing the effective ascorbate compound with lutetium-177 and/or tetraazacyclododecane tetra-acetic acid-octreotate (DOTATATE) and/or a complex of lutetium-177 and/or tetraazacyclododecane tetra-acetic acid-octreotate (DOTATATE). In such methods, the ascorbate compound may be an ascorbate salt, such as sodium ascorbate.

In certain preferred aspects, the admixture of lutetium-177 and tetraazacyclododecane tetra-acetic acid-octreotate (DOTATATE) is heated. In particular aspects, the admixture is heated for 60 minutes or less, for 50 minutes or less, for 40 minutes or less, for 30 minutes or less, for 20 minutes or less, or for 15 minutes or less.

In certain preferred aspects, the admixture of lutetium-177 and tetraazacyclododecane tetra-acetic acid-octreotate (DOTATATE) is heated at about 80° C.±10° C., or at about 80° C.±5° C.

In certain preferred aspects, the present methods include cooling the admixture following heating.

In certain preferred aspects, following the admixing, the complex of lutetium-177 and tetraazacyclododecane tetra-acetic acid-octreotate (DOTATATE) is mixed with a formulation composition. Preferably, the formulation composition is an aqueous composition that includes one or more stabilizer compounds. The formulation composition suitably includes one or more stabilizer compounds present in an amount of 5, 6, 7, 8, 9 or 10 mg/mL or greater, in an amount of 20 mg/mL or greater, in an amount of 30 mg/mL or greater, in an amount of 40 mg/mL or greater, or in an amount of 50, 60, 70, 80 or 90 mg/mL or greater.

In certain preferred aspects, a formulation composition further comprises one or more sequestering agents.

In certain preferred aspects, incorporation of lutetium-177 into or with tetraazacyclododecane tetra-acetic acid-octreotate (DOTATATE) to provide $^{177}$Lu-DOTATATE is preferably greater than 98 mole percent, or greater than 99 mole percent based on the molar equivalent of lutetium-177 used in the incorporation reaction.

In certain preferred aspects, an acidic aqueous formulation of lutetium-177 is admixed with the tetraazacyclododecane tetra-acetic acid-octreotate (DOTATATE). Preferably, a hydrogen halide or acid halide aqueous formulation of lutetium-177 is admixed with the tetraazacyclododecane tetra-acetic acid-octreotate (DOTATATE). For example, a hydrochloride acid aqueous formulation of lutetium-177 is admixed with the tetraazacyclododecane tetra-acetic acid-octreotate (DOTATATE).

In an aspect, provided is $^{177}$Lu-DOTATATE obtainable, or obtained by the methods described herein.

In an aspect, provided is a pharmaceutical composition including $^{177}$Lu-DOTATATE as described herein. Preferably, radiochemical purity of the composition is 95% or greater for 3 days or more at 25° C., or 95% or greater for 4 days or more at 25° C., or 95% or greater for 5 days or more at 25° C. As referred to herein, radiochemical purity is preferably assessed via HPLC analysis.

In an aspect, provided is a single dosage kit including $^{177}$Lu-DOTATATE or pharmaceutical composition described herein. Moreover, provided is a multiple dosage kit including the $^{177}$Lu-DOTATATE or pharmaceutical composition described herein.

In an aspect, provided is a method of treating a subject suffering from cancer. The method includes administering to the subject an effective amount of $^{177}$Lu-DOTATATE or pharmaceutical composition described herein.

In certain aspects, the subject is suffering from a neuroendocrine tumor. In certain aspects, the subject is suffering from neuroendocrine tumors that originate from foregut, hindgut, midgut, lung, ovary, medulla, adrenal medulla, adrenal, kidney, pituitary, thyroid or paraganglia.

In certain aspects, the subject is suffering from a gastroenteropancreatic neuroendocrine tumor (GEP-NET), foregut, midgut and hindgut neuroendocrine tumors.

In certain aspects, the subject is suffering from unresectable or metastatic neuroendocrine tumor(s).

In certain aspects, the methods include identifying a patient for treatment by assessing neuroendocrine tumors of the patient to be somatostatin receptor positive, for example with $^{68}$Ga-DOTATATE and a positron emission tomography scan.

Use of the $^{177}$Lu-DOTATATE compound and compositions to treat a disease or disorder as disclosed herein is also provided.

Further provided are methods for manufacture of a medicament that comprises the $^{177}$Lu-DOTATATE compound and composition to treat a disease or disorder as disclosed herein.

Other aspects of the invention are disclosed infra.

BRIEF DESCRIPTION OF THE FIGURE

FIG. 6 (includes FIGS. 6A-6B).

DETAILED DESCRIPTION

Figure 1:
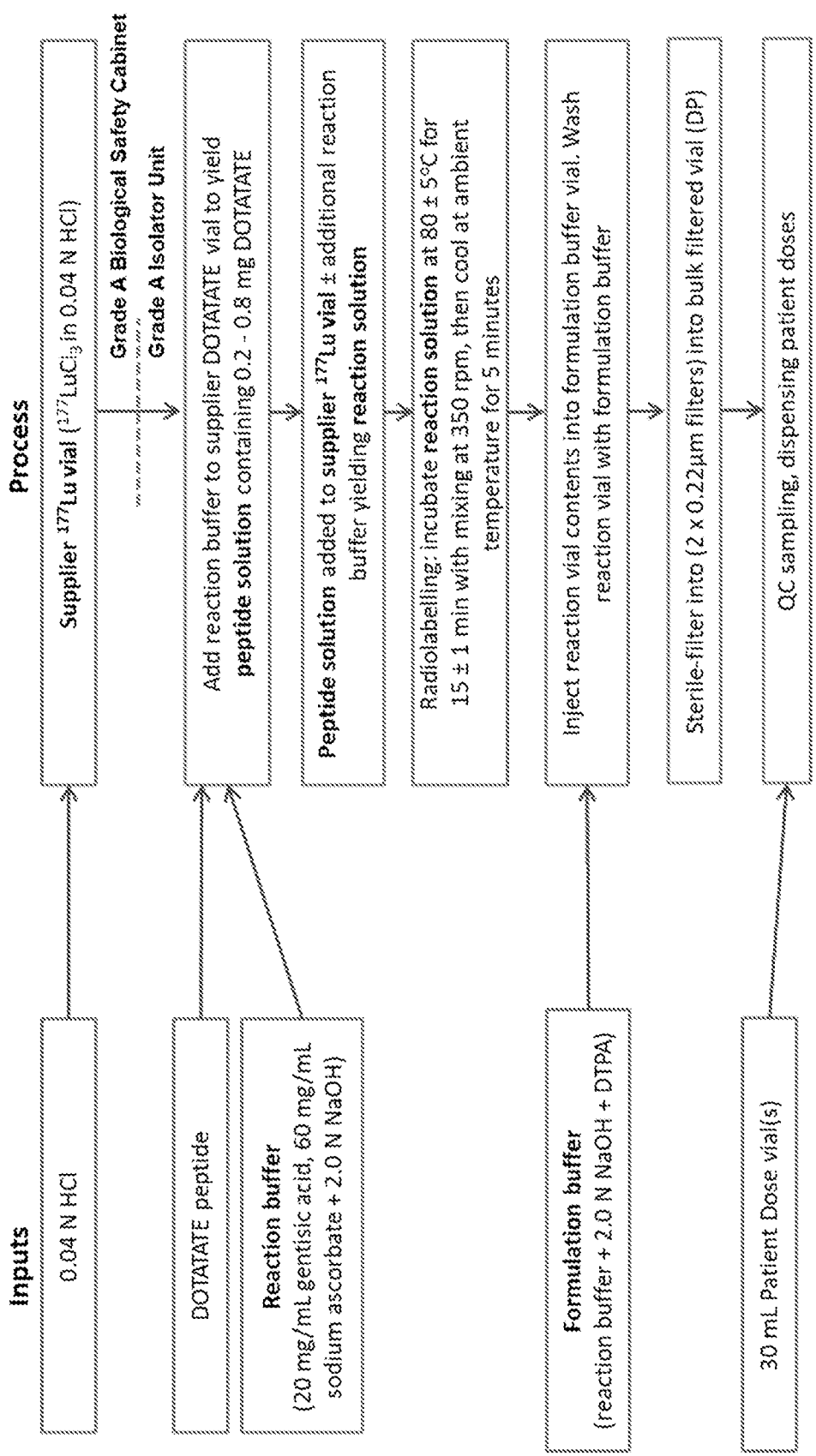
FIG. 1 shows exemplary processes for manufacturing $^{177}$Lu-DOTATATE.

As discussed above, $^{177}$Lu-DOTATATE is a lutetium-177 ($^{177}$Lu$^{3+}$) complex of the compound 1

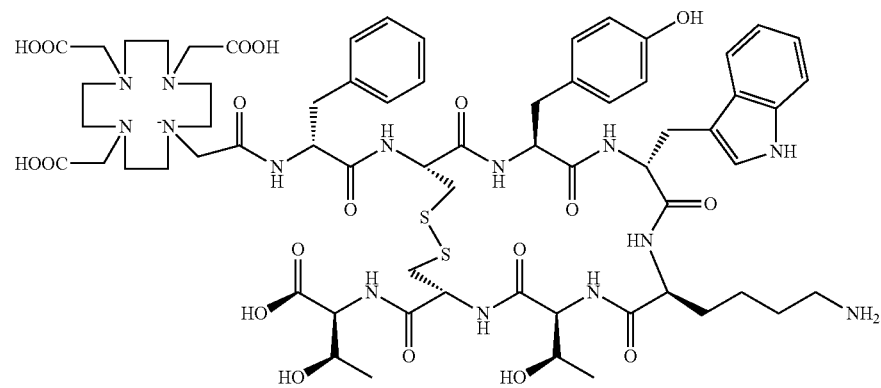

and may be represented by the following structure 2:

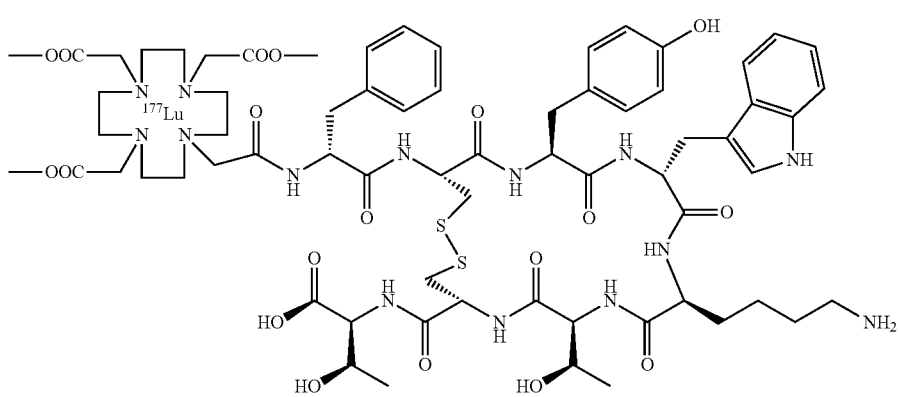

$^{177}$Lu-DOTATATE is also represented with a chemical (IUPAC) name of $^{177}$Lu-tetraazacyclododecane tetra-acetic acid-octreotate or $^{177}$Lu-4,7,10-Tricarboxymethyl-1,4,7,10-tetraaza-cyclododecan-1-yl-acetyl-D-Phe-Cys-Tyr-D-Trp-Lys-Thr-Cys-Thr-OH. $^{177}$Lu-DOTATATE has a molecular formula of $C_{65}H_{90}[^{177}Lu]N_{14}O_{19}S_2$ and a molecular weight (average molecular weight) of 1610.61 g/mol.

The present invention, including compounds, methods, and pharmaceutical compositions/formulations will be described with reference to the following definitions which, for convenience, are set forth below. Unless otherwise specified, the below terms used herein are defined as follows:

Definitions

As used herein, the term "a," "an," "the" and similar terms used in the context of the present invention (especially in the context of the claims) are to be construed to cover both the singular and plural unless otherwise indicated herein or clearly contradicted by the context.

The language "and/or" is used herein as a shorthand notation to represent the expression "and," describing the combination of items, as well as "or," describing the items in the alternative form.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

The term "about", as used herein, means an acceptable margin of error for a particular value, which depends in part on how the value is measured or determined. In certain aspects, "about" as used herein will be understood by persons of ordinary skill in the art to mean up to plus or minus 20% of the particular term. In further aspects, "about" as used herein will be understood by persons of ordinary skill in the art to mean up to plus or minus 10% of the particular term.

As used herein, the term "substantially pure" means sufficiently homogeneous to appear free of readily detectable impurities as determined by standard analytical methods, such as thin layer chromatography (TLC), gel electrophoresis, high performance liquid chromatography (HPLC), nuclear magnetic resonance (NMR), and mass spectrometry (MS); or sufficiently pure such that further purification would not detectably alter the physical and chemical properties, or biological and pharmacological properties, such as enzymatic and biological activities, of the substance. In certain aspects, "substantially pure" refers to a collection of molecules, wherein at least about 55%, about 60%, about 65%, about 70%, about 75%, about 80%, about 85%, about 90%, about 95%, about 97%, about 98%, about 98.5%, about 99%, about 99.5% or about 99.9% or greater of the molecules are a single compound, including a racemic mixture or a single stereoisomer thereof, as determined by standard analytical methods.

As used herein, and unless otherwise specified, the terms "treat," "treating" and "treatment" refer to the eradication or amelioration of a disease, disorder, or condition, or of one or more symptoms associated with the disease, disorder or condition. In certain aspects, the terms refer to minimizing the advancement or worsening of the disease, disorder, or condition resulting from the administration of a formulation of the invention to a patient with such a disease, disorder, or condition. In some aspects, the terms refer to the administration of a formulation provided herein, after the onset of symptoms of the particular disease, disorder, or condition. The terms "treat," "treating", "treatment", or the like, as used herein covers the treatment of a disease, disorder, or condition in a subject, e.g., a mammal, and includes at least one of: (i) inhibiting the disease, disorder, or condition, i.e., partially or completely halting its progression; (ii) relieving the disease, disorder, or condition, i.e. causing regression of symptoms of the disease, disorder, or condition, or ameliorating a symptom of the disease, disorder, or condition; and (iii) reversal or regression of the disease, disorder, or condition, preferably eliminating or curing of the disease, disorder, or condition. In a particular embodiment the terms "treat," "treating", "treatment", or the like, covers the treatment of a disease, disorder, or condition in a mammal, e.g., a primate, e.g., a human, and includes at least one of (i), (ii), and (iii) above. As is known in the art, adjustments for age, body weight, general health, sex, diet, time of administration, drug interaction and the severity of the condition may be necessary, and will be ascertainable with routine experimentation by one of ordinary skill in the art based on the invention described herein.

As used herein, the terms "subject", and "patient" are used interchangeably. The terms "subject" and "patient" refer to an animal such as a mammal including non-primates (e.g., a cow, pig, horse, sheep, rabbit, guinea pig, rat, cat, dog, and mouse) and primates (e.g., a monkey, chimpanzee and a human). In a particular embodiment, the subject is a human.

Syntheses

In an aspect, $^{177}$Lu-DOTATATE (including structure 2) can be prepared by complexing or incorporating $^{177}$Lu (Lutetium 177) or halide thereof such as $^{177}$LuCl$_3$ with DOTATATE (including structure 1 below):

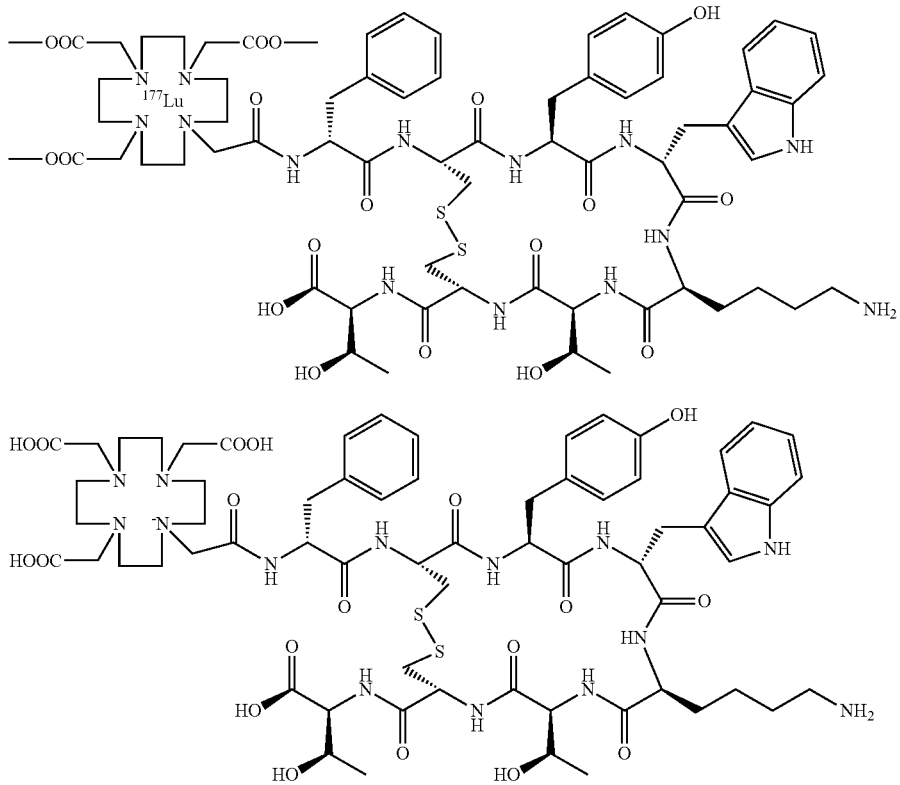

The compound 1 DOTATATE may be suitably formed as described previously such as in Raheem et al. *Bioconjugate Chem.* 2020. https://doi.org/10.1021/acs.bioconjchem.0c00325. The compound 1 DOTATATE is also commercially available.

It is understood that $^{177}$Lu-DOTATATE as referred to herein includes the above structure 2 as well as other complexes of $^{177}$Lu-DOTATATE. For instance, references herein to $^{177}$Lu-DOTATATE include compounds that generally correspond to structure 2 but where the $^{177}$Lu substantially complexes to other portions or moieties (such as one or more other nitrogens) of the DOTATATE molecule than as depicted in 2 above. References to $^{177}$Lu-DOTATATE also may include other stereoisomers than those shown in 1 and 2 above, although the stereoisomer depicted in 1 and 2 is preferred.

To synthesize $^{177}$Lu-DOTATATE, a salt form of lutetium-177 ($^{177}$Lu) can be admixed with DOTATATE in an incorporation reaction. The $^{177}$Lu suitably may be carrier-added or more preferably no-carrier-added (n.c.a.) lutetium-177. To facilitate incorporation (e.g. complexing including chelating) of lutetium-177 with DOTATATE compound, preferably an admixture of the compounds is in the presence of one or more stabilizer compounds.

In an aspect, the method of preparing $^{177}$Lu-DOTATATE includes a step of admixing lutetium-177 and tetraazacyclododecane tetra-acetic acid-octreotate (DOTATATE) in the presence of one or more stabilizer compounds; and forming a complex of lutetium-177 and tetraazacyclododecane tetra-acetic acid-octreotate (DOTATATE).

Preferably, as discussed, in an incorporation reaction, the one or more stabilizer compounds are present in an amount of 7, 8, 9 or 10 mg/mL or greater. In certain aspects, the one or more stabilizer compounds are present in an incorporation reaction in an amount of 20 mg/mL or greater. In certain aspects, the one or more stabilizer compounds are present in an incorporation reaction in an amount of 30 mg/mL or greater. In certain aspects, the one or more stabilizer compounds are present in an incorporation reaction in an amount of 40 mg/mL or greater. In certain aspects, the one or more stabilizer compounds are present in an incorporation reaction in an amount of 50, 60 or 70 mg/mL or greater.

Preferably, the one or more stabilizers comprise one or more ascorbate compounds. For example, the ascorbate compound may include an ascorbate salt such sodium ascorbate.

Preferably, the one or more stabilizers comprise one or more gentisate compounds. For example, the gentisate compound may include, but not limited to, gentisic acid.

Preferably, the one or more stabilizers in an incorporation reaction comprise one or more gentisate compounds in an amount of at least 5, 6, 7, 8, 9 or 10 mg/mL and one or more ascorbate compounds in an amount of at least 10, 20, 30, 40 or 50 mg/mL. In certain aspects, the one or more stabilizers in an incorporation reaction comprise one or more gentisate compounds in an amount of at least 15 mg/mL and one or more ascorbate compounds in an amount of at least 40 mg/mL.

Preferably, the admixture of lutetium-177 and tetraazacyclododecane tetra-acetic acid-octreotate (DOTATATE) is heated. In certain aspects, the admixture is heated for 20 minutes or less. In certain aspects, the admixture is heated for 15 minutes or less.

Preferably, the admixture of lutetium-177 and tetraazacyclododecane tetra-acetic acid-octreotate (DOTATATE) is heated at a temperature of about 80° C.±10° C. In certain aspects, the admixture lutetium-177 and tetraazacyclododecane tetra-acetic acid-octreotate (DOTATATE) is heated at a temperature of about 80° C.±5° C.

The method further includes cooling the admixture of lutetium-177 and tetraazacyclododecane tetra-acetic acid-octreotate (DOTATATE) following heating.

In certain aspects, following the admixing, the complex of lutetium-177 and tetraazacyclododecane tetra-acetic acid-octreotate (DOTATATE) is mixed with a formulation composition. Preferably, the formulation composition is an aqueous composition that comprises one or more stabilizer compounds. In certain aspects, the formulation composition comprises one or more stabilizer compounds in an amount of 5, 6, 7, 8, 9 or 10 mg/mL or greater. In certain aspects, the formulation composition comprises one or more stabilizer compounds in an amount of 20 mg/mL or greater. In certain aspects, the formulation composition comprises one or more stabilizer compounds present in an amount of 30 mg/mL or greater. In certain aspects, the formulation composition comprises one or more stabilizer compounds present in an amount of 40 mg/mL or greater. In certain aspects, the formulation composition comprises one or more stabilizer compounds present in an amount of 50, 60 or 70 mg/mL or greater.

In certain aspects, the formulation composition further includes one or more sequestering agents.

Preferably, incorporation of lutetium-177 into or with tetraazacyclododecane tetra-acetic acid-octreotate (DOTATATE) to provide $^{177}$Lu-DOTATATE is greater than 98 mole percent based on the molar equivalent of lutetium-177 used in the incorporation reaction. In certain aspects, incorporation of lutetium-177 into or with tetraazacyclododecane tetra-acetic acid-octreotate (DOTATATE) to provide $^{177}$Lu-DOTATATE is greater than 99 mole percent based on the molar equivalent of lutetium-177 used in the incorporation reaction.

Preferably, an acidic aqueous formulation of lutetium-177 is admixed with the tetraazacyclododecane tetra-acetic acid-octreotate (DOTATATE). In a certain embodiment, a hydrogen halide or acid halide aqueous formulation of lutetium-177 is admixed with tetraazacyclododecane tetra-acetic acid-octreotate (DOTATATE).

Preferred preparations of $^{177}$Lu-DOTATATE may include one or more and preferably each of the following steps:

1. Provide lutetium-177 in a vial or other container that can serve as a reaction vessel. The lutetium-177 suitably may be present in an aqueous acidic formulation, for example, an HCl formulation.

2. Admix DOTATATE peptide with an aqueous buffer composition (Reaction Buffer) that contains one or more ascorbate compounds (e.g., sodium ascorbate) and optionally, one or more gentisate compound (e.g., gentisic acid).

3. Admix the DOTATATE peptide from step 2 with the lutetium-177 composition of step 1. For example, the DOTATATE peptide composition from step 2 can be added to the vial that contains the lutetium-177.

4. The admixture of DOTATATE peptide and lutetium-177 then can be heated preferably with agitation, for example shaking with heating at 70-90° C., more typically 75-85° C. for up to 6, 7, 8, 9, 10, 11, 12, 13, 14, 15, 16, 17, 18, 19 or 20 minutes.

5. After completion of the heating treatment, the admixture from step 4 above is allowed to cool for about 0.1, 0.25, 0.5, 1, 2, 3, 4, 5, 6 or 7 minutes at or below room temperature (e.g. 25° C.). Cooling may be facilitated by adding an aqueous composition (Formulation Composition) containing one or more ascorbate compounds (e.g. sodium ascorbate) and optionally, one or more gentisate compounds (e.g., gentisic acid) to the vial containing the admixture of step 4. The Formulation Composition added to the admixture may be at or below room temperature (e.g. 25° C.).

6. The admixture from step 5 then may be transferred to a vessel containing an aqueous composition (may be the same Formulation Composition as used in step 5) that comprises one or more ascorbate compounds and, in certain systems, one or more gentisate compounds. The mixture may be sterile filtered such as through one or more 0.22 μm filter and transferred to a container such as a syringe, vial or IV bag. Desired dosages can be dispensed for administration to a patient preferably within or example 5, 4, 3, 2, 1 or 0.5 days from completion of step 6.

In certain aspects, the preparation of $^{177}$Lu-DOTATATE includes the exemplary process shown in FIG. 1. For example, $^{177}$Lu vial may contain $^{177}$LuCl$_3$ in 0.04 N HCl. A specifically preferred Reaction Buffer may suitably include 19 mg/mL gentisic acid, 57.3 mg/mL sodium ascorbate, and 3.7 mg/mL NaOH. A specifically preferred Formulation Composition may include 18.7 mg/mL gentisic acid, 56.1 mg/mL sodium ascorbate, 5.3 mg/mL NaOH, and 0.4 mg/mL diethylenetriaminepentaacetic acid (DTPA).

Other compositions shown in Examples are incorporated herein.

Pharmaceutical Compositions

In a further aspect, pharmaceutical compositions are provided.

Preferred pharmaceutical compositions may include an aqueous composition including 1) a complex of lutetium-177 and DOTATATE and 2) one or more ascorbate compounds.

Additional preferred pharmaceutical compositions may include an aqueous composition including 1) a complex of lutetium-177 and DOTATATE and 2) one or more gentisate compounds.

Still further preferred pharmaceutical compositions may include an aqueous composition including 1) a complex of lutetium-177 and DOTATATE; 2) one or more gentisate compounds; and 3) one or more ascorbate compounds.

Yet further preferred pharmaceutical compositions may include an aqueous composition including 1) a complex of lutetium-177 and DOTATATE; 2) one or more gentisate compound; 3) one or more ascorbate compounds; and 4) one or more sequestering agents.

Preferably, the radiochemical purity of a pharmaceutical composition is at least 95% where the composition is maintained at 25° C. or less and for 3, 4, or 5 days or more following preparation of the composition.

In certain preferred aspects, the pharmaceutical composition is free of unchelated lutetium-177 in an amount of not more than 2, 1.5, 1.0 or 0.5 weight % based on total weight of the pharmaceutical composition, such as may be determined by radiometric detection (including HPLC radiometric detection), where the composition is maintained at 25° C. or less and such purity levels are exhibited for 3 days or more following preparation of the composition.

In additional preferred aspects, the pharmaceutical composition is free of radiochemical impurities in an amount of not more than 5, 4, 3.5, 3, 2.5, 2, 1.5, 1 or 0.5 weight % based on total weight of the pharmaceutical composition, such as may be determined by radiometric detection (including HPLC radiometric detection), where the pharmaceutical composition is maintained at 25° C. or less and such purity levels of the pharmaceutical composition are exhibited for 3 days or more following preparation of the pharmaceutical composition.

In yet still additional preferred aspects, the pharmaceutical composition is free of chemical impurities in an amount of not more than 5, 4, 3, 2, 1 or 0.5 weight % based on total weight of the pharmaceutical composition, such as may be determined by HPLC/UV analysis, where the composition is maintained at 25° C. or less and such purity levels are exhibited for 3, 4 or 5 days or more following preparation of the pharmaceutical composition.

In yet still additional preferred aspects, the pharmaceutical composition is 1) free of unchelated lutetium-177 in an amount of not more than 2, 1.5, 1.0 or 0.5 weight % (such as may be determined by radiometric detection (including HPLC radiometric detection)); 2) free of radiochemical impurities in an amount of not more than 5, 4, 3.5, 3, 2.5, 2, 1.5, 1 or 0.5 weight % (such as may be determined by radiometric detection (including HPLC radiometric detection); and 3) free of chemical impurities in an amount of not more than 5, 4, 3, 2, 1 or 0.5 weight % (such as may be determined by HPLC/UV analysis), with all weight % based on total weight of the pharmaceutical composition, and where the pharmaceutical composition is maintained at 25° C. or less and such purity levels are exhibited for 3 days or more following preparation of the pharmaceutical composition.

In certain preferred aspects, purity levels, including radiochemical purities as referred to herein are determined by HPLC analysis, including radio-HPLC.

In certain aspects, the pharmaceutical composition is formulated for parenteral administration, such as intravenous, intramuscular, intradermal, subcutaneous, intrathecal or intraperitoneal administration. For example, the pharmaceutical composition is formulated for intravenous, intramuscular, subcutaneous or intradermal injection. In preferred aspects, the pharmaceutical composition is formulated for intravenous administration. In typical aspects, the pharmaceutical composition may be administered in a form of a pharmaceutical aqueous solution.

In certain aspects, the pharmaceutical composition is an aqueous solution, dispersion or other admixture such as for injection and comprises $^{177}$Lu-DOTATATE and preferably 1) one or more ascorbate compounds; and/or 2) one or more gentisate compounds.

In certain preferred aspects, a pharmaceutical aqueous solution, dispersion or admixture is provided that includes: 1) a complex of lutetium-177 and DOTATATE; and 2) at least one stabilizer compound that preferably can inhibit radiolytic degradation of the composition during storage following preparation of the complex. $^{177}$Lu-DOTATATE is suitably present in a concentration that it provides a volumetric radioactivity of at least 100 MBq/mL, preferably of at least 250 MBq/mL, or at least 300 or 400 MBq/mL within 1, 2, 3 or 4 days following preparation. In certain aspects, $^{177}$Lu-DOTATATE is present in a concentration that it provides a volumetric radioactivity of from 100 to 1000 MBq/mL, preferably from 250 to 800 MBq/mL within 1, 2, 3 or 4 days following preparation.

In certain aspects, the one or more stabilizer compounds may be present in a total concentration of at least 5 mg/mL, preferably at least 10, 20, 30, 40, 50, 60, 70, 80, 90 or 100 mg/mL of an aqueous pharmaceutical composition.

In certain aspects, the one or more stabilizer compounds may be present in a total concentration of at least 10 mg/mL, or at least 20, 30, 40, 50, 60 or 70 mg/mL of an aqueous pharmaceutical composition.

In additional certain aspects, the one or more stabilizer compounds may be present in a total concentration of at least 20 or 25 mg/mL, or at least 30, 40, 50, 60 or 70 mg/mL of an aqueous pharmaceutical composition.

In certain aspects, the one or more stabilizer compounds are one or more of gentisic acid (2,5-dihydroxybenzoic acid) or salts thereof, ascorbic acid (L-ascorbic acid) or salts thereof (e.g. sodium ascorbate), methionine, N-acetyl-L-methionine, N-acetyl-L-cysteine, histidine, melatonin, ethanol, or Se-methionine, preferably ascorbic acid or salts thereof.

In certain aspects, the one or more stabilizer compounds are one or more of 1) gentisic acid (2,5-dihydroxybenzoic acid) or salts thereof or 2) ascorbic acid (L-ascorbic acid) or salts thereof (e.g. sodium ascorbate).

In certain aspects, the pharmaceutical aqueous formulation has a shelf life of at least 24 hours at about 25° C. or less, at least 48 hours at about 25° C. or less, at least 72 hours at about 25° C. or less, or from 24 hours to 120 hours at about 25° C. or less, from 24 hours to 96 hours at about 25° C. or less, from 24 hours to 84 hours at about 25° C. or less, from 24 hours to 72 hours at about 25° C. or less, in particular a shelf life of 72 hours at about 25° C. or less.

In certain aspects, one, two or three total distinct stabilizer compounds are present during the complex formation of lutetium-177 and DOTATATE, preferably in an amount to result in a concentration of from 5 mg/mL or more of the one, two or three or more stabilizer compounds. As discussed, preferably at least one of the stabilizer compounds will be an ascorbate compound.

In certain aspects, as discussed, one or more stabilizer compounds may be added after formation of the complex of lutetium-177 and DOTATATE, for example upon completion of heating of an admixture of lutetium-177 and DOTATATE. As discussed, preferably at least one of the stabilizer compounds added after formation of $^{177}$Lu-DOTATATE will be an ascorbate compound, for example where such stabilizer compound(s) are added upon temperature reduction at the conclusion of a heating step. In certain aspects, a gentisate compound also will be added after formation of $^{177}$Lu DOTATATE, for example where such stabilizer compound(s) are added upon temperature reduction at the conclusion of a heating step. In that regard, the addition of an aqueous formulation containing one or more stabilizers promptly after heating is terminated can act to cool the $^{177}$Lu DOTATATE reaction mixture.

In certain aspects, a pharmaceutical aqueous solution may further include a sequestering agent, for example added after formation of a complex of lutetium-177 and DOTATATE, suitably to remove uncomplexed lutetium-177. Suitable sequestering agents may include for example one or more aminopolycarboxylic acids, e.g. ethylenediaminetetraacetic acid (EDTA) and diethylenetriaminepentaacetic acid (DTPA) or a salt thereof, suitably in an amount to result in a concentration of from 0.01 to 0.50 mg/mL of the aqueous $^{177}$Lu-DOTATATE composition.

In a particularly preferred aspect, $^{177}$Lu-DOTATATE is provided as a sterile solution for intravenous use. A single-dose vial suitably will contain a dose of from 3.6±10% GBq to 11.1±10% GBq $^{177}$Lu-DOTATATE. Four treatment cycles, represented by one injection per treatment cycle results in a cumulative dose of from 14.4±10% GBq to 44.4±10% GBq.

Preferably, the pH range of the $^{177}$Lu-DOTATATE solution is 4.5 to 8.5. In a particularly preferred aspect, the pH range of the $^{177}$Lu-DOTATATE solution is 5 to 7.

Methods of Treatment

As discussed, use of $^{177}$Lu-DOTATATE (including 2 above) is provided to treat cancers, including cancers originated from foregut (e.g., stomach or duodenum), hindgut (e.g., left colon or rectum), midgut (e.g., jejunum, ileum, right colon, or appendiceal), lung, pancreas, and other organs (e.g., ovary, medulla, adrenal medulla, adrenal (pheochromocytoma), kidney, pituitary, thyroid or paraganglia).

In particular, $^{177}$Lu-DOTATATE (including 2 above) may be used to treat neuroendocrine tumors, including to reduce neuroendocrine tumor size.

In such methods, $^{177}$Lu-DOTATATE (including 2 above) can be administered to a subject such as a human in an amount effective to treat the cancer (e.g., reduction of tumor size), such as at a dose of about 1 or 2 GBq to about 15 GBq or 20 GBq or more per treatment cycle, and in certain aspects from 3.6 GBq to about 11.1 GBq per treatment cycle, and can be suitably administered from a unit dose in a vial or a syringe or as a bulk solution in a vial or a syringe prepared from a cold-kit prepared with lutetium-177 at a local or central radiopharmacy or through cGMP central manufacturing. Total dose administered for therapy including 4 treatment cycles is about 14.4 GBq to about 40.8 GBq or 44.4 GBq.

The effective amount of the $^{177}$Lu-DOTATATE radiopharmaceutical administered to a patient will generally be determined by considering the patient record. However, the effective amount suitably may be within a range of about at a dose of about 1 or 2 GBq to about 15 GBq or 20 GBq or more per dose, more typically about 3.6 GBq to 11.1 GBq per dose, for example, about 3.6, 4, 4.5, 5, 5.5, 6, 6.5, 7, 7.4, 8, 8.5, 9, 9.5, 10, 10.5, 11, 11.1 GBq per dose, or any range between two of the above values. The dose can be administered from a unit dose in a vial or a syringe or as a bulk solution in a vial or a syringe prepared from a cold-kit prepared with lutetium-177 at a local or central radiopharmacy or through cGMP central manufacturing.

If necessary or desirable, the treatment may involve more than one administration of an effective amount of $^{177}$Lu-DOTATATE. It is generally beneficial to repeat the administration of $^{177}$Lu-DOTATATE to the subject after 7 to 56 days, such as at a 4 to 8 week interval.

In a particularly preferred protocol, the $^{177}$Lu-DOTATATE dosage form is a sterile aqueous solution that is administered by intravenous injection. The dosing regimen may include multiple infusions such as 4 infusions at effective dosages such as from 3.6 GBq±10% to 11.1 GBq±10% each, administered about 4, 5, 6, 7 or 8 weeks apart.

In certain aspects, the methods include assessing neuroendocrine tumors of a patient to be somatostatin receptor positive, for example with $^{68}$Ga-DOTATATE and a positron emission tomography scan.

Personalized Dosing

In further aspects, dosing protocols may be utilized to provide dosing amounts for a specified patient based on one or more of the patient's characteristics.

In particular, $^{177}$Lu-DOTATATE may be administered in dosage amounts based on dosimetry assessments. For example, following administration of $^{177}$Lu-DOTATATE, the patient may be assessed by SPECT (e.g. 3D SPECT-CT imaging) and planar scans or other analysis to allow individualized dosimetry. Multiple scans may be performed, for example at approximately 4, 24 and 72 hours following dosing, or at a single time point or other schedule. The scans can be used to determine doses absorbed such as by tumors, kidneys and bone marrow of the patient. Based on that assessment, additional dosing of the patient can be modified, in particular either increased or decreased to enhance efficacy or safety.

Additionally, a patient's glomerular filtration rate (GFR) also may be assessed typically by a determination of creatinine (Cr) clearance.

Preferably, a patient receiving $^{177}$Lu-DOTATATE will be assessed both by dosimetry and Cr clearance/GFR. By such a combined assessment, patients may be dosed with $^{177}$Lu-DOTATATE at a GFR of 40 mL/min and as low as 30 mL/min.

Combination Therapy $^{177}$Lu-DOTATATE (including 2 above) suitably may be administered to a subject in conjunction or combination with one or more other therapeutic agents, particularly one or more other chemotherapeutic agents.

In one aspect, a subject may receive treatment with $^{177}$Lu-DOTATATE in combination with a regime of one or more somatostatin compounds, such as octreotide (e.g. Sandostatin) or lanreotide (e.g. Somatuline Autogel).

A subject also may receive treatment with $^{177}$Lu-DOTATATE in combination with a regime of one or more anticancer agents, for example capecitabine, temozolomide, steptozotocin, 5-fluroouracil, cisplatin, carboplatin, etoposide, and/or doxorubicin.

As used herein, the term "in combination" in the context of the administration of a therapy to a subject refers to the use of more than one therapy for therapeutic benefit. The term "in combination" in the context of the administration can also refer to the prophylactic use of a therapy to a subject when used with at least one additional therapy. The use of the term "in combination" does not restrict the order in which the therapies (e.g., a first and second therapy) are administered to a subject. A therapy can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject in need of treatment as disclosed herein. The therapies are administered to a subject in a sequence and within a time interval such that the therapies can act together. In a particular embodiment, the therapies are administered to a subject in a sequence and within a time interval such that they provide an increased benefit than if they were administered otherwise. Any additional therapy can be administered in any order with the other additional therapy.

Packaged $^{177}$Lu-DOTATATE and Kits

As discussed above, treatment kits are also provided, including cold kits where the $^{177}$Lu-DOTATATE can be prepared shortly before administration such as in a medical facility, for example a hospital laboratory or radiopharmacy. In such a kit, DOTATATE may be provided in a vial or other container in lyophilized or other form separate from lutetium-177. The DOTATATE and lutetium-177 are reacted as disclosed herein at the medical facility to provide $^{177}$Lu-DOTATATE which then can be promptly administered to a patient.

The kit may be a single dosage kit including $^{177}$Lu-DOTATATE or pharmaceutical composition as described herein. Alternatively, the kit may be a multiple dosage kit comprising $^{177}$Lu-DOTATATE or pharmaceutical composition as described herein.

In a further aspect, packaged preparations or products of $^{177}$Lu-DOTATATE are also provided. A packaged preparation may comprise 1) $^{177}$Lu-DOTATATE and optionally 2) instructions for using $^{177}$Lu-DOTATATE for treating a cancer such as a neuroendocrine tumor. Preferably, the packaged preparation will comprise a therapeutically effective amount of $^{177}$Lu-DOTATATE.

In certain exemplary packaged preparations or products, $^{177}$Lu-DOTATATE can be packaged in suitable containers labeled, for example, for use as a therapy to treat a subject suffering from cancer e.g. a neuroendocrine tumor. The containers can include $^{177}$Lu-DOTATATE and one or more of a suitable stabilizer compounds as disclosed herein. A product can include a container (e.g., a vial or the like) containing $^{177}$Lu-DOTATATE. In addition, an article of manufacture or kit further may include, for example, packaging materials, instructions for use, syringes, delivery devices, for treating the targeted condition, such as a neuroendocrine tumor or other cancer.

A packaged system or product may also include a legend (e.g., a printed label or insert or other medium (e.g., an audio or video file) describing the product's use). The legend can be associated with the container (e.g., affixed to the container) and can describe the manner in which the compositions therein should be administered (e.g., the frequency and route of administration), indications therefor, and other uses. The compositions can be ready for administration (e.g., present in dose-appropriate units), and may include one or more additional pharmaceutically acceptable adjuvants, carriers or other diluents.

The following non-limiting examples are illustrative.

Example 1: $^{177}$Lu-DOTATATE Manufacturing

Table 1 describes all input materials into the manufacturing process

TABLE 1

| Ingredient | Quantity per batch |
|---|---|
| $^{177}$LuCl$_3$ (in 0.04N HCl) | ≤88.4 GBq[1] |
| DOTATATE peptide | 0.2-0.8 mg[2] |
| 0.04N HCl solution            1N HCl | <1 mL |
| Sterile Water for Injection, USP | |
| Reaction Buffer[3] | |
| (19 mg/mL gentisic acid, 57.3 mg/mL sodium ascorbate, 3.7 mg/mL NaOH) | |
| Gentisic acid | 0.6-2.4 mL, particularly |
| Sodium ascorbate, USP/EP | 1.2 mL |
| Sterile Water for Injection, USP | |
| 2.0N NaOH | |
| Formulation Buffer | |
| (18.7 mg/mL gentisic acid, 56.1 mg/mL sodium ascorbate, 5.3 mg/mL NaOH, 0.4 mg/mL DTPA) | |
| Reaction buffer | 6.95-115.6 mL |
| 2.0N NaOH | |
| Diethylenetriamine pentaacetic (DTPA) acid | |

[1]At start of synthesis
[2]Depending on number of doses/batch
[3]Also a component of the Formulation Buffer Table 2 below describes the ingredients found in the final formulated drug product.

TABLE 2

| Ingredient | Quantity[1,2] | Role in formulation |
|---|---|---|
| $^{177}$Lu-DOTATATE | ~80.3 GBq[3] | Drug substance |
| | ≤0.96 GBq/mL[3] | |
| Gentisic acid | 16-19 mg/mL | Radioprotectant and buffer |
| Sodium ascorbate, USP/EP | 49-56 mg/mL | Radioprotectant and buffer |
| Sterile Water for Injection, USP | 15.5-118 mL | Diluent |
| DTPA | 0.3-0.4 mg/mL | Chelator of free [Lu-177] to minimize physiological uptake |
| Sodium Hydroxide, USP-NF | 4.6-5.1 mg/mL | Adjustment of buffer pH |

[1]Total batch volume = 16-120 mL
[2]Ranges depend on batch size and volume required to yield target radioactivity concentration
[3]At time of calibration (TOC), defined as 07:00 ET on day of manufacture Fabrication Process Step 1 described in this section takes place in a Grade A biological safety cabinet. All subsequent steps described in this section take place within a Grade A shielded isolator. All solutions, including Reaction Buffer and Formulation Buffer, are prepared in a Grade C clean room. In summary, in the incorporation reaction, the DOTATATE peptide is mixed with reaction buffer and $^{177}$LuCl$_3$, followed by heating and shaking to form the drug complex substance.

The heater/shaker undergoes installation, operation and performance qualification prior to use. Qualification has confirmed that the required temperature and shaking conditions for the incorporation reaction (radiolabeling) can be maintained for the specified time period, as described in Step 4 below.

The amount of DOTATATE peptide used (Step 2) is based on the total amount of $^{177}$Lu-DOTATATE activity (itself based on the number and timing of patient doses) and the volume required to yield a radioactive concentration of ≤0.96 GBq/mL at time of calibration (TOC). The TOC is defined as 07:00 ET on the day of manufacture (DOM).

1. Depending on the amount of $^{177}$Lu starting activity required, the appropriate volume of 0.04 N HCl is added to the supplier vial containing $^{177}$LuCl$_3$ in 0.04 N HCl to bring the total volume to
   a. 1000 μL (if 160-320 μs of DOTATATE peptide are used)
   b. 2000 μL (if 480-640 μs of DOTATATE peptide are used)
2. 1-4×750 μL volume(s) of DOTATATE peptide are prepared in reaction buffer. The solution is gently agitated to ensure complete dissolution of the peptide. Each 750 volume of DOTATATE peptide solution contains 200 μg DOTATATE.
3. If only 1× or 3×750 μL aliquots of DOTATATE solution are required, an additional 1×600 μL volume of reaction buffer is prepared.
4. The reaction solution is prepared by adding 600 μL volumes of DOTATATE solution from Step 2 (and if applicable reaction buffer from Step 3) to the supplier vial from Step 1 (containing diluted $^{177}$LuCl$_3$). The total reaction solution volume is 2.2 mL (160-320 μg of peptide) or 4.4 mL (480-640 μg of peptide).
5. Using the qualified and pre-heated heater/shaker, the reaction solution is heated at 80±5° C. for 15±1 min with shaking at 350 rpm.
6. The reaction solution vial containing the drug substance is allowed to cool at room temperature for at least 5 min.

Subsequent steps consist of transferring the drug substance (in reaction buffer) through a tandem 2×0.22 µm sterile filter chain, to a 100 mL sterile bulk vial containing formulation buffer, and aseptic dispensing of the final drug product into the final container closure. These steps are accomplished using a dispensing apparatus consisting of a series of stopcocks to which various tubing, syringes, vials and needles are attached to facilitate transfer and dispensing of the drug product. Steps 7-10 take place within a Grade A shielded isolator unit.

7. The $^{177}$Lu-DOTATATE drug substance is immediately transferred from the reaction vial, through a tandem 2×0.22 µm sterile filter chain, to a 100 mL bulk vial that contains (post-reaction vial rinsing) 6.95-115.6 mL of formulation buffer. This step forms the drug product and represents end of synthesis (EOS).
8. Samples are removed from this vial for sterility and QC testing.
9. Patient doses are dispensed into final 30 mL container closures.

The total synthesis time, from Step 3 to Step 7 described above, is approximately 120 min.

Figure 2:
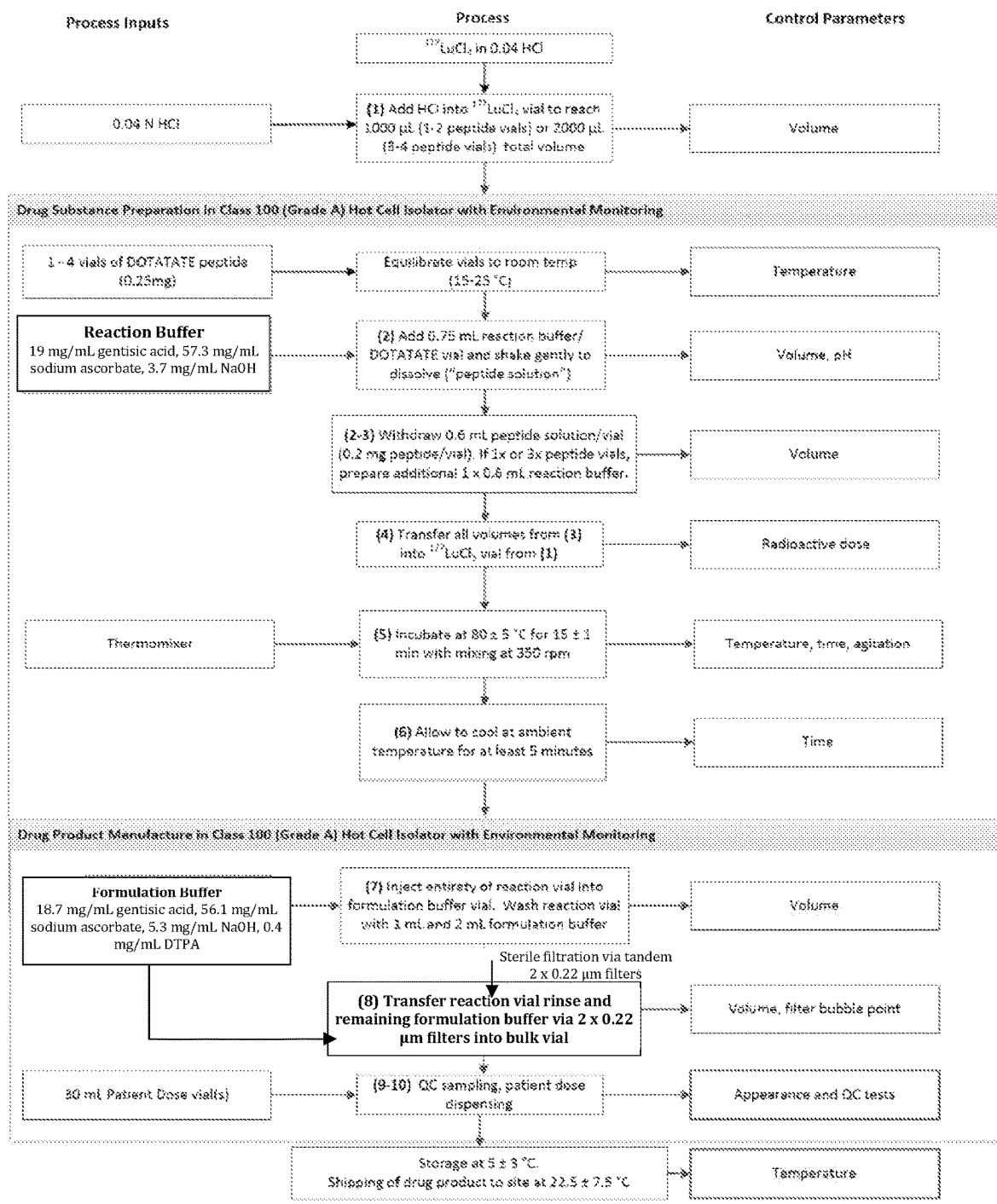
FIG. 2 shows a flow chart for an exemplary fabrication process of Example 1.

FIG. 2 shows a flow chart for a preferred exemplary fabrication process.

Example 2: Treatment Protocol

A human patient with neuroendocrine tumors is selected for treatment after their tumors have been shown to be somatostatin receptor positive with $^{68}$Ga-DOTATATE and a positron emission tomography scan.

$^{177}$Lu-DOTATATE in a sterile aqueous solution as set forth in Table 2 of Example 1 above is administered by intravenous injection to the patient. Single-dose vials are used that contain from 3.6±10% GBq to 11.1±10% GBq $^{177}$Lu-DOTATATE. The $^{177}$Lu-DOTATATE is administered over four treatment cycles, with one injection per treatment cycle that provides a cumulative dose of from 14.4 GBq to 44.4 GBq.

Example 3

Materials and Methods

An Eppendorf Thermomixer C, 96-well Eppendorf Microplates and ThermoFisher 96-well plate sealing tape were used for small scale reaction screening. A VWR heating block was used for scaled up reactions. A Waters Acquity Arc UHPLC with a radioactivity detector and an Acquity QDa mass detector were used for analysis. A Thermo Scientific Acclaim 120 C18 column (150×3 mm, 120 Å, 3 µm) was used for chromatographic separation. An Eckert & Ziegler AR-2000 Radio-TLC Imaging Scanner was used for radio-iTLC analysis.

The $^{nat}$Lu-DOTATATE reference standard was purchased from ABX advanced biochemical compounds GmbH (Radeberg Germany) and the DOTATATE precursor was obtained from Auspep Clinical Peptides.

Radio-iTLC Method

Agilent iTLC-SA chromatography paper was used for radio-iTLC analysis. The mobile phase used for chromatographic separation was 20% CH$_3$OH in 0.1M citrate buffer. The sample volume spotted on the paper was 1 µL. The migration distance was 9 cm.

Instrument Settings

| | |
|---|---|
| Column temperature | 40° C. |
| Mobile phase | A: H$_2$O + 0.1% TFA |
| | B: CH$_3$CN + 0.1% TFA |
| System wash & seal/needle wash | 50% CH$_3$CN/H$_2$O |

-continued

| | |
|---|---|
| Flow rate | 0.6 mL/minute |
| Autosampler tray temperature | Ambient temperature |
| UV Detector parameters | Single λ = 220 nm |
| | Sampling Rate: 1 point/sec |
| Radiometric Detector parameters | eSatin: 60 Hz, Sampling Rate: 2 points/second, Scale Factor 1000. Bioscan FC: Detector PMT, Integration Time 1 sec. ERM: 12 CPM |

HPLC Mobile Phase Gradient

| Time | % A | % B | Gradient Curve |
|---|---|---|---|
| 0 | 85 | 15 | 6 (Linear) |
| 17.0 | 68 | 32 | 6 (Linear) |
| 17.5 | 40 | 60 | 6 (Linear) |
| 20.5 | 40 | 60 | 6 (Linear) |
| 21.0 | 85 | 15 | Re-equilibration |
| 28.0 | 85 | 15 | |

Buffer Development

The volume of 1M NaOH or 1M HCl to reach the desired pH in the incorporation reaction admixture or the final drug complex product mixture was determined experimentally.

Incorporation Reaction Condition Screening Experiment
Non-Variable Parameters

For the incorporation reaction screening experiments, the following components were added to each reaction well:

| Component | Volume (µL) |
|---|---|
| $^{175/177}$LuCl$_3$ in 0.04N HCl | 45.5 |
| Reaction buffer (see below) + precursor peptide (DOTATATE) | 54.5 |

The peptide concentration in the reaction mixture was 90.9 µg/mL. The radioactive concentration (RAC) of each incorporation (radiolabelling) reaction was 1 µCi/mL at the start of the experiment. $^{175}$LuCl$_3$ was spiked into the reaction to reach the Lu/precursor molar ratio in a comparable manufacturing process with $^{177}$LuCl$_3$ at a specific activity of 3.8 GBq/µg, using a 7.8 GBq input activity.

Variable Parameters

Screening of incorporation reaction conditions was performed with the following reaction variables of the Reaction buffer as referred to above and used in 54.5µ:

| Reaction buffer components | Value |
|---|---|
| Sodium ascorbate (mg/mL)** | 100, 50, 10 |
| Gentisic acid (mg/mL)** | 15, 7, 0 |

| Reaction buffer and incorporation reaction parameters | Value |
|---|---|
| pH* | 4, 5, 6 |
| Incorporation reaction temperature (° C.) | 45, 60 |
| Incorporation reaction time (minutes) | 10, 15, 30 |

*pH specified as tested in final incorporation reaction (radiolabeling) mixture.
**Sodium ascorbate and gentisic acid concentrations specified for incorporation reaction buffer (before addition of $^{175/177}$LuCl$_3$ in 0.04N HCl).

Variable Parameters for the Second Round of Incorporation Reaction Condition Screening The second round of incorporation reaction condition screening was performed with the following reaction variables. Not all permutations of these variables were tested.

| Reaction parameter | Value |
| --- | --- |
| pH* | 4.5, 5 |
| Sodium ascorbate (mg/mL)** | 100, 75 |
| Gentisic acid (mg/mL)** | 15, 7, 0 |
| Reaction temperature (° C.) | 45, 60 |
| Reaction time (minutes) | 30, 60 |

*pH specified as tested in final incorporation reaction (radiolabeling) mixture.
**Sodium ascorbate and gentisic acid concentrations specified for incorporation reaction (radiolabeling) buffer (before addition of $^{175/177}$LuCl$_3$ in 0.04N HCl).

Evaluation of Incorporation Reaction Condition Screening Experiments

For the initial incorporation reaction condition screening experiment, each experiment was evaluated by radio-iTLC immediately after the reaction. The various time-points were sampled from the same reaction volume and spotted onto the iTLC paper to quench the reaction. For the second round of incorporation reaction experiments, radio-iTLC and radio-HPLC analysis was performed.

Formulation Condition Screening Experiment

Incorporation Reaction

A single incorporation reaction was performed and aliquoted into different formulation buffers for the formulation condition screening experiment. The following parameters were used for the incorporation reaction:

| Incorporation reaction mixture component | Value |
| --- | --- |
| Precursor peptide (DOTATATE) concentration* | 90.9 µg/mL |
| Radioactive ($^{177}$Lu) concentration* | 3.36 GBq/mL |
| Sodium ascorbate** | 100 mg/mL |
| Gentisic acid** | 0 mg/mL |
| Incorporation reaction parameter | Value |
| pH | 5 |
| Reaction mixture volume | 0.416 mL |
| Reaction temperature | 60° C. |
| Reaction time | 30 minutes |

*Parameter specified in final incorporation reaction mixture.
**Parameter specified for incorporation reaction (radiolabeling) buffer (before addition of $^{177}$LuCl$_3$ in 0.04N HCl to reach the final incorporation reaction mixture).

Non-Variable Formulation Parameters

For the formulation condition screening experiments, the following components were added to each reaction well:

| Component | Volume (µL) |
| --- | --- |
| Incorporation reaction mixture | 22.0 |
| Formulation buffer | 59.0 |

The Following Parameters were Held Constant for Each Formulation Condition Test:

| Parameter | Value |
| --- | --- |
| DTPA* | 0.29 mg/mL |
| Radioactive concentration* | 0.912 GBq/mL |
| Reaction mixture dilution ratio | 1:3.68 (Reaction mixture to final product volume) |

*Parameter specified in final product mixture.

Variable Formulation Parameters

Screening of formulation conditions (to provide $^{177}$Lu-DOTATATE pharmaceutical compositions) was performed with the following reaction variables:

| Reaction parameter* | Value |
| --- | --- |
| pH | 5, 6 |
| $^{177}$Lu-DOTATATE pharmaceutical composition components | Value |
| Sodium ascorbate (mg/mL) | 100, 75, 50 |
| Gentisic acid (mg/mL) | 18, 11, 0 |

*Parameter specified as tested in final product mixture.

Evaluation of Formulation Screen Experiments

The formulation screen experiments were analyzed by radio-iTLC on day 0, 1, 3 and 5. The sample was analyzed by radio-HPLC on day 5.

Scale Up Experiments

Incorporation Reaction Parameters

Two incorporation reactions were performed. The following components were added to each reaction vessel:

| Component | Volume (µL) |
| --- | --- |
| $^{177}$LuCl$_3$ in 0.04N HCl | 500 |
| Reaction buffer (see incorporation reaction #1 (L1) and (L2) #2 values below) + 100 µg precursor peptide (DOTATATE) | 600 |

Formulation Parameters

The following components parameters were used for the two incorporation reactions:

| | Incorporation reaction #1 (L1) Value | Incorporation reaction #2 (L2) Value |
| --- | --- | --- |
| Component | | |
| Radioactive concentration | 3.36 GBq/mL | 3.36 GBq/mL |
| Sodium ascorbate* | 100 mg/mL | 100 mg/mL |
| Gentisic acid* | 0 mg/mL | |
| Parameter | | |
| pH | 5 | 5 |
| Reaction time | 30 minutes | 60 minutes |
| Reaction temperature | 60° C. | 45° C. |

*Parameter specified for incorporation reaction buffer (before addition of $^{177}$LuCl$_3$ in 0.04N HCl to reach the final incorporation reaction mixture). 100 mg/mL sodium ascorbate in the buffer corresponds to 54 mg/mL in the incorporation reaction.

Two different formulation conditions were used for each of the two incorporation reactions (L1 and L2). The following components were combined to obtain four different final products:

| Component | Volume (µL) |
| --- | --- |
| Incorporation reaction mixture (L1 and L2) | 500 |
| Formulation buffer (F1 and F2) | 1360 |

The following parameters were used for the two different product formulations:

|  | Formulation #1 (F1) Value | Formulation #2 (F2) Value |
|---|---|---|
| Component |  |  |
| Radioactive concentration | 0.913 GBq/mL | 0.913 GBq/mL |
| Sodium ascorbate* | 75 mg/mL | 50 mg/mL |
| Gentisic acid* | 15 mg/mL | 15 g/mL |
| Parameter |  |  |
| PH | 6 | 6 |
| DTPA | 0.29 mg/mL | 0.29 mg/mL |
| Reaction mixture dilution ratio | 1:3.72 | 1:3.72 |

*Parameter specified for radiolabeling buffer (before addition of $^{177}$LuCl$_3$ in 0.04N HCl to reach the final incorporation reaction mixture)

Evaluation of Scale Up Experiments

Each of the two incorporation reaction mixtures were formulated with the two formulation specifications to generate four samples, L1F1, L2F2, L2F1, and L2F2. The four products were tested by radio-iTLC and radio-HPLC on day 0, 1, 2 and 5. The products were stored at room temperature over the course of the 5-day study.

Results and Discussion

Incorporation Reaction Optimization

Incorporation reaction screening was conducted to evaluate the effect of pH, sodium ascorbate concentration, gentisic acid concentration, reaction temperature and reaction time on radiometal ($^{177}$Lu) incorporation (Table 3).

TABLE 3

Incorporation condition screening variables.

|  | Value |
|---|---|
| Incorporation reaction component |  |
| Sodium ascorbate (mg/mL) | 100, 50, 10 |
| Gentisic acid (mg/mL) | 15, 7, 0 |
| Reaction parameter |  |
| pH | 4, 5, 6 |
| Reaction temperature (° C.) | 45, 60 |
| Reaction time (minutes) | 10, 15, 30 |

Figure 3:
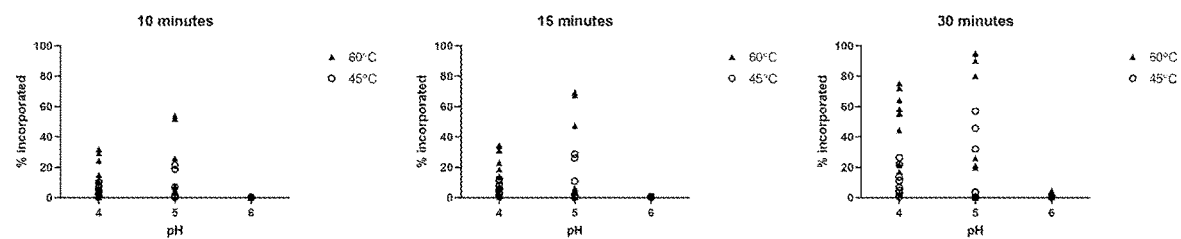
FIG. 3 shows effect of reaction time, temperature, and pH on % incorporation of Lu-177 as disclosed in Example 3.

Optimal Incorporation Reaction Achieved at pH 5, 30 Min Reaction Time, and 60° C. Reaction Temperature Analysis of the reactions by radio-iTLC indicated that optimal incorporation reaction (radiolabeling) was achieved at pH 5. The reaction was worse at pH 4 and did not notably proceed at pH 6 (FIG. 3). Performing the reaction at higher temperature and for a longer duration allowed for more efficient incorporation of Lu-177.

Sodium Ascorbate Improves Incorporation Reaction

Figure 4:
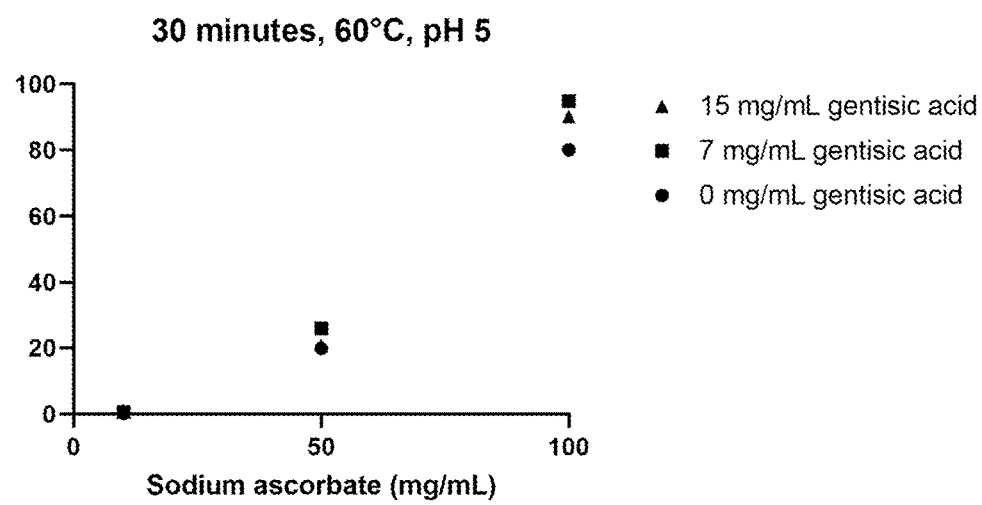
FIG. 4 shows effect of sodium ascorbate and gentisic acid on % incorporation of Lu-177 as disclosed in Example 3.

The presence of sodium ascorbate had a significant beneficial effect on radiometal ($^{177}$Lu) incorporation in the test reactions. The reactions with 100 mg/mL of sodium ascorbate in the reaction buffer (corresponding to 54 mg/mL in the radiolabeling mixture) had the highest % $^{177}$Lu incorporation as measured by radio-iTLC. Gentisic acid was well tolerated in the reaction at all concentrations tested. See results set forth in FIG. 4.

Second Round of Incorporation Reaction (Radiolabeling) Screening Experiments

Eight incorporation reactions were performed and evaluated by radio-iTLC and radio-HPLC (Table 4 below).

TABLE 4

Incorporation reaction conditions for reactions tested in second round of radiolabeling screening experiments.

| Sample # | pH | Reaction temp (° C.) | Reaction time (min) | Sodium ascorbate (mg/mL) | Gentisic acid (mg/mL) | Radio-iTLC (% incorporation ± SD) |
|---|---|---|---|---|---|---|
| 1 | 5 | 60 | 30 | 100 | 15 | 96.9 ± 0.4 |
| 2 | 5 | 60 | 30 | 100 | 7 | 99.1 ± 0.1 |
| 3 | 5 | 60 | 30 | 100 | 0 | 98.9 ± 0.1 |
| 4 | 4.5 | 60 | 30 | 100 | 7 | 98.8 ± 0.2 |
| 5 | 5 | 60 | 30 | 75 | 7 | 98.9 ± 0.1 |
| 6 | 4.5 | 60 | 30 | 100 | 0 | 96.1 ± 4.2 |
| 7 | 5 | 60 | 30 | 75 | 0 | 99.0 ± 0.2 |
| 8 | 5 | 45 | 60 | 100 | 7 | 98.1 ± 0.9 |

Figure 5:
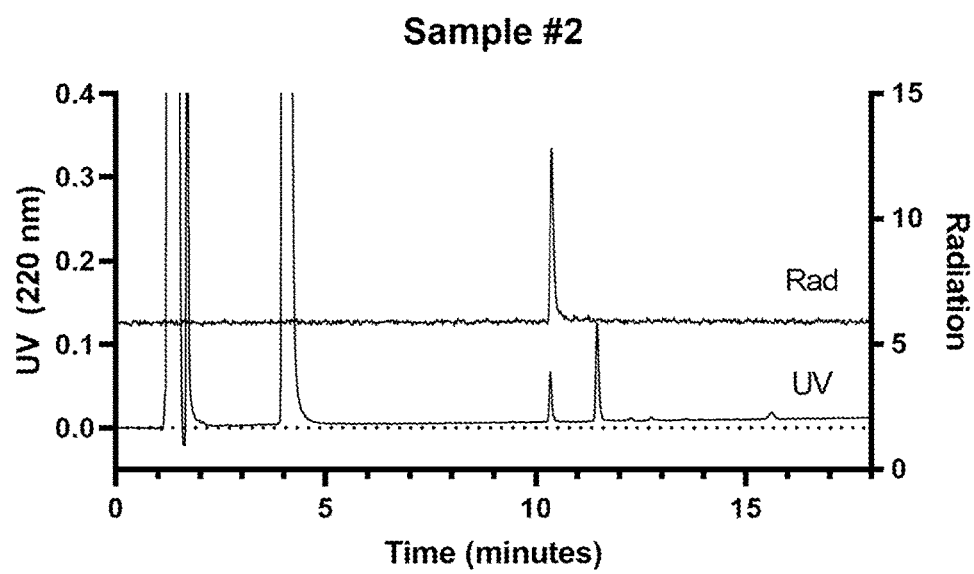
FIG. 5. Radio-HPLC chromatogram of sample 2 analysis (Example 3). Overlay of the UV (220 nm) with the radiation detector trace. $^{177}$Lu-DOTATATE eluted at $t_R$=10.2 minutes and the precursor peptide eluted at $t_R$=11.4 minutes as disclosed in Example 3.

For all samples, the only radioactive peak that was observed was $^{177}$Lu-DOTATATE (FIG. 5), although due to the trace amount of activity used in the reaction (1 µCi/mL), the radiation detector signal was very low. Significant tailing of the product peak was also observed with an elevating baseline after each injection, which prevented the injection of more material per sample injection. This problem carried into subsequent experiments and was ultimately resolved by replacing the fluid path line (Waters) in the radiation detector.

Figures 6A, 6B:
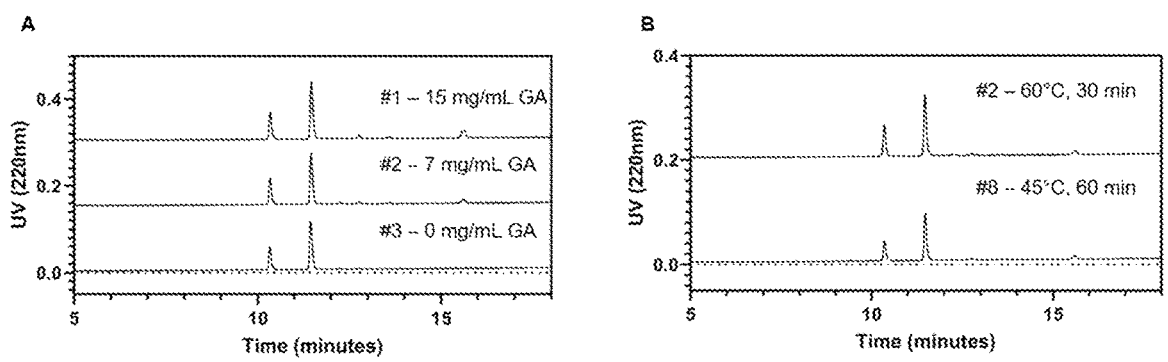
FIG. 6A: HPLC analysis of chemical impurities in reactions with various amounts of gentisic acid.
FIG. 6B. HPLC analysis of chemical impurities in reaction heated at different temperatures. $^{177}$Lu-DOTATATE eluted at $t_R$=10.2 minutes and the precursor peptide eluted at $t_R$=11.4 minutes.

Comparison of the UV trace between samples #1, #2 and #3 indicated that increased chemical impurities are detected in samples containing more gentisic acid (see FIG. 6A). Analysis of gentisic acid by HPLC indicated that some of these peaks are impurities that are present in the gentisic acid material as received. Comparison of the UV traces between samples #2 and #8 show increased amounts of chemical impurities when a higher reaction temperature is used. Control experiments showed that new impurities form from gentisic acid and/or its initial impurities when heated in solution.

Due to the increase chemical purity with higher concentrations of sodium ascorbate (100 mg/mL) and lower concentrations of gentisic acid (0 mg/mL), sample #3 labeling conditions was selected for further investigation in formulation screening tests.

Formulation Evaluation

Formulation screening was conducted to evaluate the effect of pH, sodium ascorbate concentration and gentisic acid concentration on the stability of $^{177}$Lu-DOTATATE. Each sample was tested by radio-iTLC on days 0, 1, 3 and 5 (Tables 5-7 below).

TABLE 5

Formulation screening iTLC results for samples with 100 mg/mL of sodium ascorbate.

| | | Sodium ascorbate-100 mg/mL | | | |
|---|---|---|---|---|---|
| | Gentisic acid | Radio-iTLC % Lu labeling | | | |
| pH | (mg/mL) | Day 0 | Day 1 | Day 3 | Day 5 |
| 5 | 25 | 97.9 | 98.2 | 95.6* | 20.7* |
| 5 | 15 | 97.4 | 98 | 99.1* | 98.4* |
| 5 | 0 | 99 | 97.5 | 98.8 | 97.5 |
| 6 | 25 | 98.8 | 98.3 | 98.7 | 98 |
| 6 | 15 | 98.4 | 98.6 | 98.5 | 97.1 |
| 6 | 0 | 98.6 | 98.7 | 98.7 | 98.7 |

*On Day 3, limited buffer observed in wells A1, A2, B1. Possibly due to evaporation from incorrect sealing of plate in top left corner.

TABLE 6

Formulation screening iTLC results for samples with 75 mg/mL of sodium ascorbate.
Sodium ascorbate-75 mg/mL

| | Gentisic acid | Radio-iTLC % Lu labeling | | | |
|---|---|---|---|---|---|
| pH | (mg/mL) | Day 0 | Day 1 | Day 3 | Day 5 |
| 5 | 25 | 96.9 | 98.2 | 97.5* | 98.4* |
| 5 | 15 | 99.1 | 98.2 | 98.1 | 97.9 |
| 5 | 0 | 98.1 | 98 | 98.1 | 97.4 |
| 6 | 25 | 98.6 | 98.2 | 98.4 | 98.1 |
| 6 | 15 | 98.7 | 98.2 | 98.9 | 97.9 |
| 6 | 0 | 98.5 | 98.3 | 99 | 98.2 |

*On Day 3, limited buffer observed in wells A1, A2, B1.

TABLE 7

Formulation screening iTLC results for samples with 50 mg/mL of sodium ascorbate.
Sodium ascorbate-50 mg/mL

| | Gentisic acid | Radio-iTLC % Lu labeling | | | |
|---|---|---|---|---|---|
| pH | (mg/mL) | Day 0 | Day 1 | Day 3 | Day 5 |
| 5 | 25 | 97.3 | 98.5 | 98.5 | 98.5 |
| 5 | 15 | 98.1 | 98.7 | 98 | 98 |
| 5 | 0 | 98.2 | 98.8 | 98.4 | 97.9 |
| 6 | 25 | 98.7 | 98.6 | 98.4 | 98.2 |
| 6 | 15 | 98.3 | 98.3 | 98.4 | 97.3 |
| 6 | 0 | 98.9 | 98.8 | 98.4 | 98.6 |

All samples were analyzed by radio-HPLC on day 5. Tailing of the product was observed which resulted in an elevated radiation detector baseline.

Figure 7:
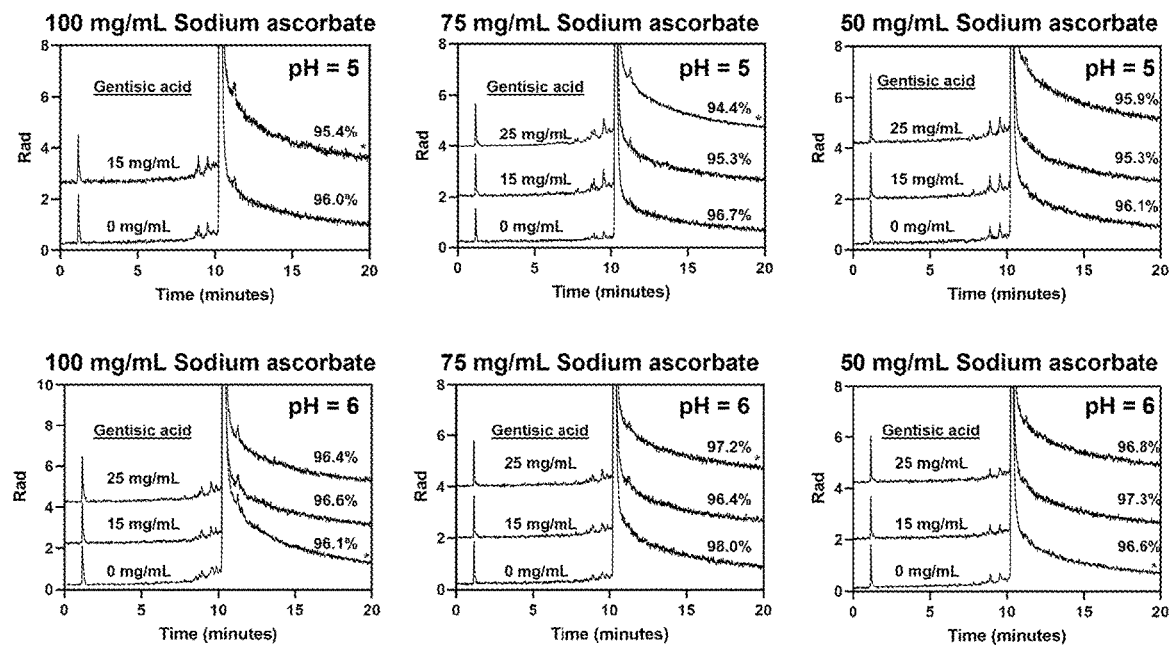
FIG. 7 shows radio-HPLC spectra of day 5 formulation screening samples as disclosed in Example 3 which follows.

While the tailing and elevated baseline of the product peak complicated interpretation of the sample spectra, some general conclusions could be made from the experiment (FIG. 7). Notably, fewer impurities were present at day 5 when the product was at pH 6. Comparison of the UV detector spectra was completed but no major differences were observed. Two formulation conditions were selected for scale up testing: F1—pH 6, sodium ascorbate 75 mg/mL, gentisic acid 15 mg/mL, and F2—pH 6, sodium ascorbate 50 mg/mL, gentisic acid 15 mg/mL.

Scale Up and Stability Testing

Two labeling conditions and two formulation conditions to generate four different products were chosen for scale up and stability testing (Tables 8-7). All samples were analyzed by radio-iTLC (Tables 10-11) and radio-HPLC on day 0, 1, 2 and 5. Tailing of the product peak was not observed after replacing the fluid path to the radiation detector. All products showed a prominent peak at the expected retention time for $^{177}$Lu-DOTATATE with several impurities eluting both before and after the product peak. These impurities were visualized by decreasing the scale on the y-axis (FIG. 7).

TABLE 8

Labeling conditions for scale up and stability test.

| Sample # | pH | Reaction temp (° C.) | Reaction time (minutes) | Sodium ascorbate (mg/mL) | Gentisic acid (mg/mL) |
|---|---|---|---|---|---|
| L1 | 5 | 60 | 30 | 100 | 0 |
| L2 | 5 | 45 | 60 | 100 | 0 |

TABLE 9

Formulation conditions for scale up and stability test.

| Sample # | pH | Sodium ascorbate (mg/mL) | Gentisic acid (mg/mL) |
|---|---|---|---|
| F1 | 6 | 75 | 15 |
| F2 | 6 | 50 | 15 |

TABLE 10

Radio-iTLC results for L1 scale up and stability tests.
L1

| | Radio-ITLC % Lu labeling | | | |
|---|---|---|---|---|
| Sample | Day 0 | Day 1 | Day 2 | Day 5 |
| F1 | 98.2 | 98.9 | 98.1 | 98.8 |
| F2 | 97.9 | 98.8 | 99.3 | 98.6 |

TABLE 11

Radio-iTLC results for L2 scale up and stability tests.
L2

| | Radio-ITLC % Lu labeling | | | |
|---|---|---|---|---|
| Sample | Day 0 | Day 1 | Day 2 | Day 5 |
| F1 | 96.7 | 97 | 97.9 | 96.3 |
| F2 | 94.8 | 97.3 | 98.1 | 97.8 |

The above results show that the synthesis of $^{177}$Lu-DOTATATE proceeds favorably at pH 5, and that using the highest incorporation reaction temperature tested (60° C.) for 30 minutes allowed for the highest degree of Lu-177 incorporation. The ascorbate compound concentration in the incorporation reaction mixture positively correlated with radiometal incorporation. The highest concentration tested (100 mg/mL in the reaction buffer=54 mg/mL in the radiolabeling mixture) led to the best results by radio-iTLC (see FIG. 4).

Formulation screening indicated that the product was stable at all conditions tested, but that a product at pH 6 results in fewer impurities than pH 5. Scale up and stability testing showed several impurities are formed in the labeling mixture and that while most of them are stable once the produce is formulated, some increase over 5 days stored at room temperature. In general, fewer impurities were observed when the product was labeled using a lower reaction temperature.

Example 4: Composition of Single Dose Batch of 177Lu-DOTATATE (97 mCi/3.59 GBq Input Lu-177)

The following compositions are prepared in accordance with procedures set forth in Examples 1 and 3 above. For all solutions, 1 g/mL density is assumed. As generally referred to herein, unless otherwise indicated, a Reaction Buffer (or similar term) is used in an incorporation reaction. As generally referred to herein, unless otherwise indicated, a Formulation Buffer (or similar term) is used to prepare $^{177}$Lu-DOTATATE pharmaceutical composition from incorporation reaction mixture.

| Quantities |||||
| --- | --- | --- | --- | --- |
| Part 1: 2N NaOH (pH 12-13) |||||
| Ingredients | Amount | Unit | Conc. ||
| Sterile Water for Injection (SWFI) | 93.30 | ml | N/A ||
| NaOH | 7.60 | g | 81.46 2.04N | mg/mL |
| Reaction Buffer |||||
| Ingredients | Amount | Unit | Conc. ||
| Sterile Water for Injection (SWFI) | 130.30 | g | N/A ||
| Sodium L-Ascorbate | 7.67 | g | 56.15 | mg/mL |
| Gentisic acid | 2.57 | g | 18.81 | mg/mL |
| 2N NaOH | 6.30 | g | 3.76 | mg/mL |
| Formulation Buffer |||||
| Ingredients | Amount | Unit | Conc. ||
| Reaction buffer | 120.90 | g | N/A ||
| DTPA | 46.30 | mg | 0.38 | mg/mL |
| 2N NaOH | 2.50 | g | 5.33 | mg/mL |
| Sodium L-Ascorbate | | g | 55.01 | mg/mL |
| Gentisic Acid | | g | 18.43 | mg/mL |

| Part 2: ||||
| --- | --- | --- | --- |
| Composition of Incorporation Reaction | volume | mg | mg/mL in Total Incorporation Reaction Volume |
| 160 ug Precursor (DOTATATE) dissolved in Reaction Buffer* | 0.60 mL | | |
| Amount Ascorbate in Reaction Buffer | | 33.69 | 21.06 |
| Amount Gentisic Acid in Reaction Buffer | | 11.29 | 7.06 |
| Amount NaOH in Reaction Buffer | | 2.25 | 1.41 |
| Volume of Lu-177 in 0.04M HCl | 1.00 mL | | |
| Total Volume = | 1.60 mL | | |

*Reaction Buffer from Part 1

| Part 3: ||||
| --- | --- | --- | --- |
| Composition of Pharmaceutical Composition Prepared from Part 2 | volume | mg | mg/mL in Pharmaceutical Composition |
| Formulation Buffer* | 6.95 mL | | |
| Amount Ascorbate in Formulation Buffer | | 382.33 | 44.72 |
| Amount Gentisic acid in Formulation Buffer | | 128.11 | 14.98 |
| Amount DTPA in Formulation Buffer | | 2.61 | 0.30 |
| Amount NaOH in Formulation Buffer | | 37.05 | 4.33 |
| Incorporation Reaction Solution** | 1.60 mL | | |
| Amount Gentisic acid in Incorporation Reaction Solution | | 11.29 | 1.32 |
| Amount Ascorbate in Incorporation Reaction Solution | | 33.69 | 3.94 |
| Amount NaOH from in Incorporation Reaction Solution | | 2.25 | 0.26 |
| Total Volume = | 8.55 mL Pharmaceutical Composition 48.66 mg/mL total ascorbate 16.30 mg/mL total gentisic acid 0.30 mg/mL DTPA 4.60 mg/mL NaOH | | |

*From Part 1
**From Part 2

Example 5: Composition of Multi-Dose Batch of 177Lu-DOTATATE (2389.2 mCi/88.4 GBq Input Lu-177)

The following compositions are prepared in accordance with procedures set forth in Examples 1, 3 and 4 above. For all solutions, 1 g/mL density is assumed.

| Quantities | | | | |
|---|---|---|---|---|
| Part 1: 2N NaOH (pH 12-13) | | | | |
| Ingredients | Amount | Unit | Conc. | |
| Sterile Water for Injection (SWFI) | 102.70 | ml | N/A | |
| NaOH | 8.40 | g | 81.79 2.04N | mg/mL |
| Reaction Buffer | | | | |
| Ingredients | Amount | Unit | Conc. | |
| Sterile Water for Injection (SWFI) | 129.70 | g | N/A | |
| Sodium L-Ascorbate | 7.93 | g | 58.36 | mg/mL |
| Gentisic acid | 2.63 | g | 19.36 | mg/mL |
| 2N NaOH | 6.18 | g | 3.72 | mg/mL |
| Formulation Buffer | | | | |
| Ingredients | Amount | Unit | Conc. | |
| Reaction buffer | 119.10 | g | N/A | |
| DTPA | 48.00 | mg | 0.40 | mg/mL |
| 2N NaOH | 2.30 | g | 5.20 | mg/mL |
| Sodium L-Ascorbate | | g | 57.25 | mg/mL |
| Gentisic Acid | | g | 18.99 | mg/mL |
| Part 2: | | | | |
| Composition of Incorporation Reaction | volume | mg | mg/mL in Total Incorporation Reaction Volume | |
| 640 ug Precursor (DOTATATE) dissolved in Reaction Buffer* | 2.40 mL | | | |
| Amount Ascorbate in Reaction Buffer | | 140.06 | 30.38 | |
| Amount Gentisic Acid in Reaction Buffer | | 46.45 | 10.08 | |
| Amount NaOH in Reaction Buffer | | 8.93 | 1.94 | |
| Volume of Lu-177 in 0.04M HCl | 2.21 mL | | | |
| Total Volume = | 4.61 mL | | | |

*Reaction Buffer from Part 1

| Part 3: | | | | |
|---|---|---|---|---|
| Composition of Pharmaceutical Composition Prepared from Part 2 | volume | mg | mg/mL in Pharmaceutical Composition | |
| Formulation Buffer* | 105.30 mL | | | |
| Amount Ascorbate in Formulation Buffer | | 6028.91 | 54.85 | |
| Amount Gentistic Acid in Formulation Buffer | | 1999.50 | 18.19 | |
| Amount DTPA in Formulation Buffer | | 41.63 | 0.38 | |
| Amount NaOH in Formulation Buffer NaOH | | 547.47 | 4.98 | |
| Incorporation Reaction Solution** | 4.61 mL | | | |
| Amount Gentisic acid in Incorporation Reaction solution | | 46.45 | 0.42 | |

-continued

| Quantities | | |
|---|---|---|
| Amount Ascorbate in Incorporation Reaction solution | 140.06 | 1.27 |
| Amount NaOH in Incorporation Reaction solution | 8.93 | 0.08 |
| Total Volume = | 109.91 mL Pharmaceutical Composition 56.13 mg/mL total ascorbate 18.61 mg/mL total gentisic acid 0.38 mg/mL DTPA 5.06 mg/mL NaOH | |

*From Part 1
**From Part 2

Example 6: Additional Compositions

The following compositions are prepared in accordance with procedures set forth in Examples 1, 3, 4 and 5 above. For all solutions, 1 g/mL density is assumed.

| Quantities | | | |
|---|---|---|---|
| 2N NaOH (pH 12-13) | | | |
| Ingredients | Amount | Unit | Conc. |
| Sterile Water for Injection (SWFI) | 98.00 | ml | N/A |
| NaOH | 8.00 | g | 81.63 mg/mL 2.04N |
| Reaction Buffer (used in incorporation reaction) | | | |
| Ingredients | Amount | Unit | Conc. |
| Sterile Water for Injection (SWFI) | 130.00 | g | N/A |
| Sodium L-Ascorbate | 7.80 | g | 57.25 mg/mL |
| Gentisic acid | 2.60 | g | 19.08 mg/mL |
| 2N NaOH | 6.24 | g | 3.74 mg/mL |
| Formulation Buffer (used to prepare $^{177}$Lu-DOTATATE pharmaceutical composition from incorporation reaction mixture) | | | |
| Ingredients | Amount | Unit | Conc. |
| Reaction buffer | 120.00 | g | N/A |
| DTPA | 47.10 | mg | 0.38 mg/mL |

-continued

| Quantities | | | |
|---|---|---|---|
| 2N NaOH | 2.40 | g | 5.27 mg/mL |
| Sodium L-Ascorbate | | g | 56.13 mg/mL |
| Gentisic Acid | | g | 18.71 mg/mL |

INCORPORATION BY REFERENCE

The entire contents of all patents, published patent applications and other disclosures cited herein are hereby expressly incorporated herein in their entireties by reference.

What is claimed is:

1. A single dosage pharmaceutical composition of 3.6 GBq to 11.1 GBq $^{177}$Lu-DOTATATE, comprising:
    (a) a complex of lutetium-177 and tetraazacyclododecane tetra-acetic acid-octreotate (DOTATATE) having 98% or greater lutetium-177 incorporation as determined by radio-iTLC;
    (b) one or more ascorbate compounds at a concentration of at least 50 mg/mL, and one or more gentistate compounds at a concentration of at least 15 mg/mL;
    wherein the pharmaceutical composition has a radioactive concentration of 0.96 GBq/mL or less and maintains a radiochemical purity of 95% or greater as determined by radio-HPLC after 5 days at 25° C.

2. The pharmaceutical composition of claim 1 wherein the complex of lutetium-177 and tetraazacyclododecane tetra-acetic acid-octreotate (DOTATATE) corresponds to the following structure:

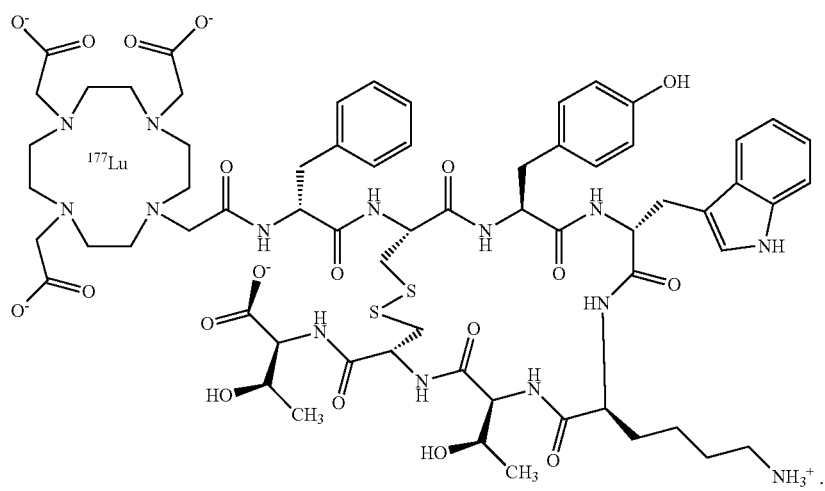

3. The pharmaceutical composition of claim 1 wherein the radiochemical purity of the composition is 95% or greater for 5 days at 25° C., as determined by both radio-HPLC analysis and radio-iTLC analysis.

4. A method for preparing $^{177}$Lu-DOTATATE, comprising:
  forming an incorporation reaction mixture comprising lutetium-177 and tetraazacyclododecane tetra-acetic acid-octreotate (DOTATATE) in the presence of one or more ascorbate compounds and one or more gentistate compounds, wherein the ascorbate compound(s) are provided at a concentration of at least 50 mg/mL in the incorporation reaction mixture, the gentistate compound(s) are provided at a concentration of at least 15 mg/mL in the incorporation reaction mixture, and the lutetium-177 is present in the incorporation reaction mixture at a radioactive concentration of about 3.36 GBq/mL,
  heating the incorporation reaction mixture to 80° C. or less thereby forming a complex of lutetium-177 and tetraazacyclododecane tetra-acetic acid-octreotate (DOTATATE) having 98% or greater lutetium-177 incorporation as determined by radio-iTLC;
  after cooling the incorporation reaction mixture, diluting the incorporation reaction mixture to form a pharmaceutical preparation comprising the complex at a radioactive concentration of 0.96 GBq/mL or less, and having a final concentration of ascorbate compound(s) of at least 50 mg/mL, and of gentistate compound(s) of at least 15 mg/mL, wherein the pharmaceutical composition maintains a radiochemical purity of 95% or greater as determined by radio-HPLC after 5 days at 25° C.

5. The method of claim 4 wherein the incorporation reaction mixture is heated for 50 minutes or less.

6. A method for treating a patient suffering from cancer, comprising:
  (a) forming an incorporation reaction mixture comprising lutetium-177 and an aqueous formulation comprising tetraazacyclododecane tetra-acetic acid-octreotate (DOTATATE) in the presence of one or more ascorbate compounds and one or more gentistate compounds, wherein the one or more ascorbate compounds are provided at a concentration of at least 50 mg/mL in the incorporation reaction mixture, and the one or more gentisate compounds are provided at a concentration of at least 15 mg/mL in the incorporation reaction mixture,
  heating the incorporation reaction mixture to 80° C. or less thereby forming a complex of lutetium-177 and tetraazacyclododecane tetra-acetic acid-octreotate (DOTATATE) having 98% or greater lutetium-177 incorporation as determined by radio-iTLC, and
  after cooling the incorporation reaction mixture, diluting the incorporation reaction mixture to form a pharmaceutical preparation comprising the complex at a radioactive concentration of 0.96 GBq/mL, and having a final concentration of ascorbate compound(s) of at least 50 mg/mL, and of gentistate compound(s) of at least 15 mg/mL,
  wherein the pharmaceutical composition maintains a radiochemical purity of 95% or greater as determined by radio-HPLC after 5 days at 25° C.; and ; and
  b) administering the pharmaceutical preparation to the patient.

7. A method of treating a subject suffering from cancer, comprising administering to the subject an effective amount of pharmaceutical composition of claim 1.

8. The single dosage pharmaceutical composition of claim 1, wherein the lutetium-177 is provided as no-carrier-added lutetium-177.

9. The method of claim 7 wherein the subject is suffering from neuroendocrine tumors.

10. A single dosage pharmaceutical composition of 3.6 GBq to 11.1 GBq $^{177}$LU-DOTATATE, comprising:
  a complex of lutetium-177 and tetraazacyclododecane tetra-acetic acid-octreotate (DOTATATE) having 98% or greater lutetium-177 incorporation as determined by radio-iTLC, being formed from an incorporation reaction carried out at a temperature of 80° C. or less in a solution including at least 15 mg/mL of one or more gentistate compounds and at least 50 mg/mL of one or more ascorbate compounds;
  which complex, after formation in the incorporation reaction, is admixed to form the pharmaceutical composition having a concentration of at least 15 mg/mL of one or more gentistate compounds and at least 50 mg/mL of one or more ascorbate compounds, wherein the pharmaceutical composition maintains after 5 days at 25° C. following preparation of the composition: i) a radioactive concentration of 0.96 GBq/mL or less and ii) a radiochemical purity of 95% or greater as determined by radio-HPLC.

11. A method of treating a subject suffering from cancer, comprising administering to the subject an effective amount of pharmaceutical composition of claim 8.

12. The single dosage pharmaceutical composition of claim 1, further including at least 0.4 mg/mL diethylenetriaminepentaacetic acid (DTPA).

13. The single dosage pharmaceutical composition of claim 10, wherein the lutetium-177 is provided as $^{177}$LuCl$_3$.

14. The single dosage pharmaceutical composition of claim 10, wherein the lutetium-177 is provided as no-carrier-added lutetium-177.

15. The single dosage pharmaceutical composition of claim 10, wherein the pharmaceutical composition further includes 0.4 mg/mL diethylenetriaminepentaacetic acid (DTPA).

16. The method of claim 4, wherein the lutetium-177 is provided as no-carrier-added lutetium-177.

17. The method of claim 4, wherein the pharmaceutical composition further includes at least 0.4 mg/mL diethylenetriaminepentaacetic acid (DTPA).

* * * * *